United States Patent
Calvani et al.

(10) Patent No.: US 7,491,825 B2
(45) Date of Patent: Feb. 17, 2009

(54) BASIC NON-PEPTIDE BRADYKININ ANTAGONISTS AND PHARMACEUTICAL COMPOSITIONS THEREFROM

(75) Inventors: Federico Calvani, Pomezia (IT); Fernando Catrambone, Pomezia (IT); Patrizia Felicetti, Pomezia (IT); Christopher Ingo Fincham, Pomezia (IT); Alessandro Giolitti, Pomezia (IT); Carlo Alberto Maggi, Pomezia (IT); Laura Quartara, Pomezia (IT); Cristina Rossi, Pomezia (IT); Rosa Terracciano, Pomezia (IT)

(73) Assignee: Menarini Ricerche S.p.A., Pomezia (IT)

( * ) Notice: Subject to any disclaimer, the term of this patent is extended or adjusted under 35 U.S.C. 154(b) by 558 days.

(21) Appl. No.: 10/516,681

(22) PCT Filed: Jun. 5, 2003

(86) PCT No.: PCT/EP03/05893

§ 371 (c)(1),
(2), (4) Date: Jul. 11, 2005

(87) PCT Pub. No.: WO03/103671

PCT Pub. Date: Dec. 18, 2003

(65) Prior Publication Data

US 2006/0205712 A1    Sep. 14, 2006

(30) Foreign Application Priority Data

Jun. 7, 2002    (IT) ........................... MI2002A1247

(51) Int. Cl.
C07D 215/38    (2006.01)
A61K 31/47    (2006.01)

(52) U.S. Cl. .................. 546/172; 514/311; 514/314

(58) Field of Classification Search ................ 546/172; 514/311, 314
See application file for complete search history.

(56) References Cited

U.S. PATENT DOCUMENTS

| 5,859,025 A | 1/1999 | Wagner et al. |
| 5,968,951 A * | 10/1999 | Dodey et al. ................ 514/311 |
| 6,063,791 A | 5/2000 | Barth et al. |
| 6,140,341 A | 10/2000 | Heitsch et al. |
| 6,211,196 B1 | 4/2001 | Heitsch et al. |

OTHER PUBLICATIONS

Akbary, A.M., Immunopharmacology, vol. 33, pp. 238-242, 1996.*
Osteoarthr. Cartil. vol. 12, S137, p. 332, 2004.*
Turner, J Allergy Clin Immunol, pp. 105-113, vol. 107 (1), 2001.*

* cited by examiner

*Primary Examiner*—D. Margaret Seaman
(74) *Attorney, Agent, or Firm*—Young & Thompson

(57) ABSTRACT

Non-peptide compounds of formula (I) having activity as specific antagonists of bradykinin (BK) B2 receptor. The compounds are chemically characterized by the presence of an alpha, alpha-disubstituted amino acid at least one amino group, free or salified, or the corresponding ammonium quaternary salt. These BK receptor antagonists are a novel class of medicaments which can be used in all the disorders in which the receptors are involved.

10 Claims, No Drawings

BASIC NON-PEPTIDE BRADYKININ ANTAGONISTS AND PHARMACEUTICAL COMPOSITIONS THEREFROM

FIELD OF THE INVENTION

The present invention relates to non-peptide, basic compounds and the derivatives thereof, having activity as specific antagonists of bradykinin (BK) B2 receptor. The BK receptors antagonists are a novel class of medicaments which can be used in all the conditions in which said receptors are involved.

More particularly, the present invention relates to non-peptide compounds which show high affinity and antagonistic activity towards B2 receptor, having general formula (I):

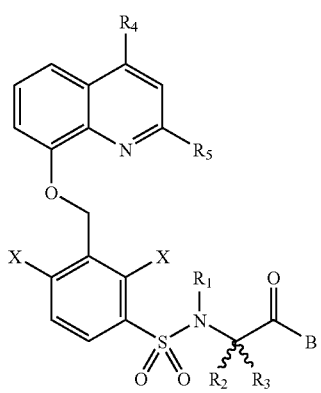

(I)

in which
- $R_1$ is a hydrogen atom or a $C_1$-$C_4$ alkyl group;
- $R_2$ and $R_3$, which can be the same or different, are a $C_1$-$C_4$ alkyl group, or $R_2$ and $R_3$, together with the carbon atom which they are linked to, form a cyclic aliphatic group having 3 to 7 carbon atoms or a heterocyclic aliphatic group having 3 to 7 atoms, one or two of which are selected from the group N, O, S and the others being C atoms;
- $R_4$ and $R_5$, which can be the same or different, are a hydrogen atom or a $C_1$-$C_4$ alkyl group;
- X is selected from the group consisting of halogen, $OR_1$, $SR_1$, CN, $C_1$-$C_4$ alkyl;
- B has at least one amino group with basic characteristics or a tetraalkylammonium group and can be selected from the group consisting of:
  $NR_6(CH_2)nNHCOY$, $NR_6(CH_2)_nN(R_6)$—Y, $NR_6(CH_2)_nN(Y)_2$, $NR_6Y$, $N(Y)_2$, $N(Y)(CH_2)_pY_1$ and from the residues:

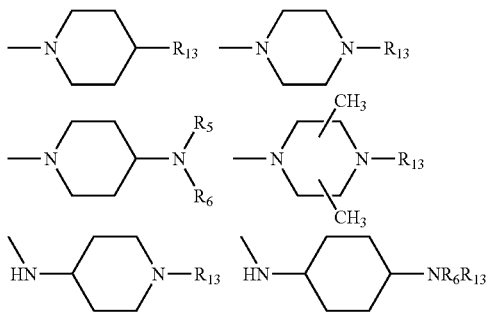

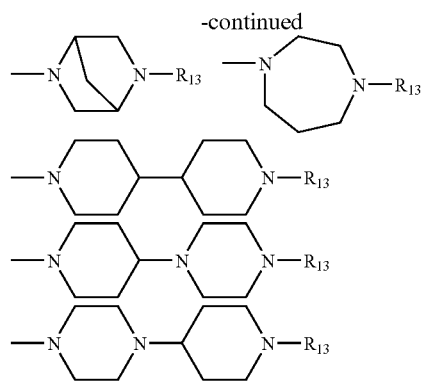

- $R_6$ is a hydrogen atom, $C_1$-$C_6$ alkyl;
- n=1-12;
- Y is selected from: hydrogen, $(CH_2)pY_1$, $(CH_2)_pNR_6Y_1$, $(CH_2)_pN(Y_1)_2$, $NR_5R_6$, —$NR_6(CH_2)_qY_1$ or from the following residues:

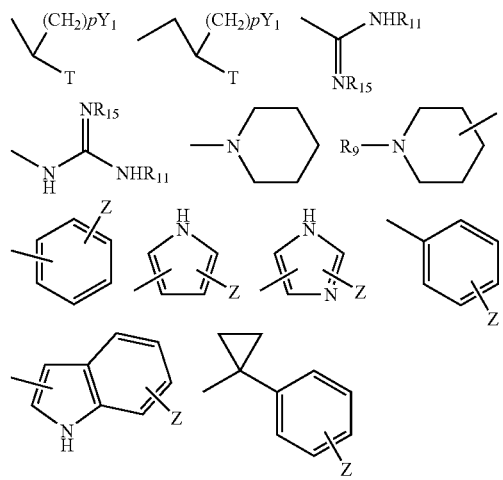

T is selected from the group of —$NR_7R_8$, —$NR_{14}R_{18}R_{19}$, —$OR_6$;

$R_7$ and $R_8$, which can be the same or different, are a hydrogen atom, a $C_1$-$C_4$ alkyl group, a cyclohexyl group, or $NR_7R_8$ together are a group selected from: i) guanidine optionally substituted with 1 or 2 $C_1$-$C_4$ alkyl or cyclohexyl groups, ii) a 5-7 membered nitrogen heterocycle optionally containing another heteroatom selected from O, N, S;

$Y_1$ is selected from the group consisting of $NR_7R_8$, $NR_{14}R_{18}R_{19}$ or from the following residues:

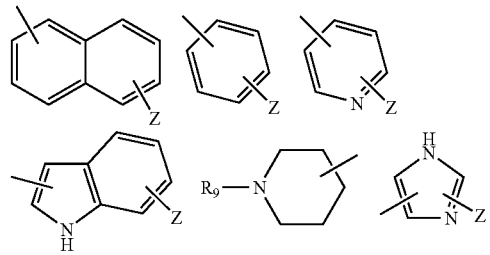

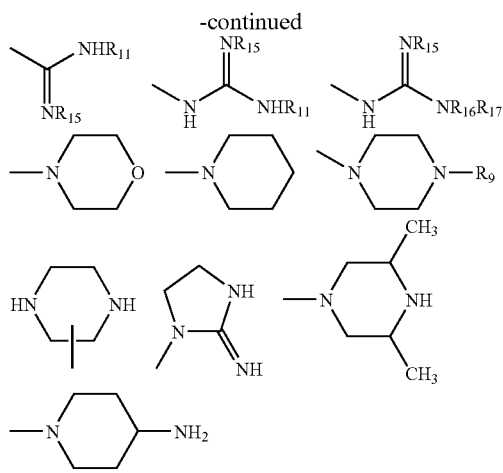

Z is selected from the group consisting of H, $C_1$-$C_6$ alkyl, $OR_6$, $SR_6$, $CF_3$, $OCOR_6$, $COR_{10}$, $NHCOR_6$, $SO_2R_6$, $SOR_6$, $CO_2R_6$, $N(R_6)_2$, Cl, Br, $NO_2$, $NH_2$, CN, F, imidazole, phenyl, amidine, guanidine, guanidyl-methyl;

$R_9$ is selected from the group consisting of hydrogen, —$(CH_2)_q$-L, wherein L is selected from the group of —OH, —$NR_5R_6$, —$NR_{14}R_{18}R_{19}$, amidine optionally substituted with 1 or 2 $C_1$-$C_4$ alkyl groups, guanidine optionally substituted with 1 or 2 $C_1$-$C_4$ alkyl groups;

$R_{10}$ is selected from the group consisting of $OR_6$, $NR_6R_{12}$;

$R_{11}$ is selected from the group consisting of hydrogen, —$(CH_2)_q$-L, —$(CH_2)_p$—$NR_4$—$(CH_2)_q$-L;

$R_{12}$ is a hydrogen atom, $C_1$-$C_6$ alkyl, $COR_6$;

$R_{13}$ is selected from the group consisting of H, $C_1$-$C_6$ alkyl, —$(CH_2)_pW(CH_2)_qY_1$, Y, —COY, —$CH_2$—Y;

$R_{15}$ is selected from the group consisting of hydrogen or straight or branched $C_1$-$C_4$ alkyl groups;

the —$NR_{16}R_{17}$ group is a 5-7 membered nitrogen aliphatic heterocycle optionally containing another heteroatom selected from O, S, N;

the —$NR_{14}R_{18}R_{19}$ group is a quaternary ammonium group in which: $R_{14}$ is selected from the group consisting of straight or branched $C_1$-$C_4$ alkyl groups, $R_{18}$ and $R_{19}$, which can be the same or different, are a straight or branched $C_1$-$C_4$ alkyl group, or —$NR_{18}R_{19}$ is a 5-7 membered nitrogen heterocycle optionally containing another heteroatom selected from O, N, S;

$W=CH_2$, O, S, $NR_4$, $N(R_4)_2$;

p=1-6, q=1-6.

The present invention also embraces the corresponding pharmacologically acceptable salts with inorganic or organic acids selected from the group of: hydrochloric, hydrobromic, hydroiodic, sulfuric, phosphoric, acetic, trifluoroacetic, propionic, oxalic, malic, maleic, succinic, malonic, aspartic, glutamic acids and possible geometrical isomers, optical isomers, due to the presence of chiral centers, or mixtures thereof, including the racemates. The symbol ∿∿∿ means that the configuration of the asymmetric carbon atoms can be either S or R. Amines are known to be mainly in the protonated form at the physiological pHs, i.e. they are in the form of quaternary ammonium, therefore this invention also comprises the analogues in which the amino nitrogen is in the form of tetraalkyl ammonium salt, i.e. the analogues in which a quaternary nitrogen independent on pH is permanently present.

PRIOR ART

Bradykinin (BK) belongs to Kinins and forms, together with Kallidin and T-Kinin, the sub-group of Kinins present in mammals. Kinins play an important role as mediators of pain and inflammation, both in the central and peripheral nervous system. They have peptide nature and bradykinin is, in particular, a nonapeptide (H-Arg[1]-Pro[2]-Pro[3]-Gly[4]-Phe[5]-Ser[6]-Pro[7]-Phe[8]-Arg[9]-OH) produced by the body in physiopathological conditions.

Two types of Kinins receptors exist, B1 and B2. The main characteristic of the B1 receptor is that it is more inducible than constitutive. It is expressed in tissues in inflammation or stress conditions. On the other hand, B2 is a constitutive receptor normally present in all tissues and ready to detect the action of the mediator during the inflammatory processes. The cascade of the enzymatic processes which induces Kinins formation and degradation was described in detail in the review by Bhoola et al.(Bhoola H. D., Figueroa C. D., Worthy K., Bioregulation of Kinins: Kallikreins, Kininogens and Kininases, Pharmacological Rev. 1992; 44:4-80). Bradykinin and Kallidin are released from their protein precursors (known as kininogens), by proteolytic enzymes named kininogenases. Among these, the main role is played by Kallikreins which however, once released by the precursor, can exert their action only for a short time as they are quickly destroyed by a series of circulating enzymes and membranes generically defined as Kininases. One of these Kininases cleaves bradykinin at the C-terminal arginine thus forming a des-Arg-BK which acts as B1 receptor agonist.

The activation of bradykinin B1 and B2 receptors induces relaxation of vasal muscles with consequent hypotension, increase in vascular permeability, contraction of smooth muscles of intestine and respiratory tract, stimulation of nociceptive neurons, alteration of ionic epithelial secretion, production of nitroxide and release of cytokines by leukocytes and eicosanoids from different cell types. As a consequence, antagonistic compounds of BK receptors can be considered a novel class of medicaments supposedly active in various disorders. Possible therapeutical applications for said antagonists are inflammatory, allergic and autoimmune disorders, such as asthma and chronic bronchitis (also induced by irritants), allergic, vasomotor and viral rhinitis, obstructive pulmonary disease (COPD), rheumatoid arthritis, chronic inflammatory diseases of the bowel (Crohn's disease and ulcerative colitis), glomerulonephritis, psoriasis, rash, acute and chronic cystitis; degenerative disorders characterized by fibrosis, such as hepatic cirrhosis, glomerulopathies and pulmonary fibrosis, arteriosclerosis; thanks to their analgesic activity, in the treatment of both acute and chronic pain, for example in burns, cephalea, insects bites, chronic pain in cancer patients; in disorders of the cardiovascular apparatus such as septic, allergic and post-traumatic shocks, and hepatic cirrhosis by hepatorenal syndrome; as anticancer and antiangiogenetics; in the treatment of hypotension and of alopecia.

Different peptide and non-peptide antagonists of bradykinin B2 receptor are known in literature.

After the discovery of the first bradykinin B2 receptor antagonist, NPC-567, in 1985, a number of peptide antagonists have been synthesized, many of them, such as Icatibant (HOE-140) and Bradycor (Deltibant, CP-0127), being already in clinical phase.

The first non-peptide B2 antagonist of bradykinin was synthesized by Sterling Winthrop in 1993, WIN 64338. Said compound, however, showed low binding activity to the human B2 receptor. Very interesting activity has been showed by quinoline and imidazopyridine derivatives claimed by Fujisawa, which starting from 1996, published pharmacological data and studies concerning the novel non-peptide antagonist FR 173657 and the analogues thereof. This compound was of paramount importance in the search for novel non-peptide B2 antagonists due to its selectivity, potency and activity after oral administration. After the publication of Fujisawa patents, similar structures were claimed in patents by Fournier and Hoechst. The compounds by Fournier also have a quinoline linked to dichlorobenzene; a substituted sulfonamide connects this part of the molecule to an aromatic ring (optionally substituted with an amidine) through a basic linker (e.g.: propylenediamine, piperazine). Fournier announced in May 1998 the start of the clinical phase I for the non-peptide B2 antagonist LF 16.0687 (review: Altamura M. et al., Regulatory Peptides, 1999, 80, 13-26).

In view of the possible advantages of the non-peptide antagonists (enzymatic and metabolic stabilities, high bioavailability) over peptide antagonists, the search for novel non-peptide B2 receptor antagonists is desirable.

DETAILED DISCLOSURE

The present invention aims at providing novel non-peptide antagonists, having a reduced conformational freedom. The present invention discloses novel compounds of non-peptide nature, i.e. straight or cyclic sulfonamido derivatives of α,α-disubstituted amino acids, of general formula (I), wherein $R_1$, $R_2$, $R_3$, $R_4$, $R_5$, X and B have the meanings defined above.

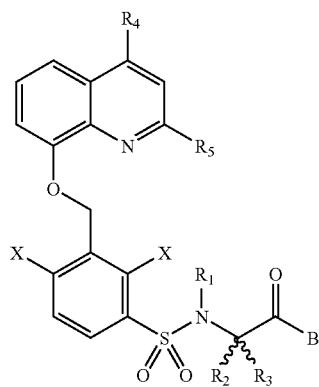

(I)

The presence of this particular category of amino acids causes limitations in the molecular conformation, thus allowing modulation and optimization of the interaction with the receptor through introduction of suitable pharmacophore groups.

These compounds are characterized both by high affinity and antagonistic activity towards human B2 receptor and remarkable metabolic stability.

The compounds of the present invention are original over the compounds claimed in patent literature (WO 97/24349, WO 98/03503) in the light of mutagenesis studies, which proved a different interaction with B2 receptor, as well as conformational studies supported by molecular modelling experiments and NMR analysis, which evidenced a defined, different conformation compared with that of analogues non containing α,α-disubstituted amino acids. In particular, a comparative study between the compounds of present invention and the analogues non-containing α,α-disubstituted amino acids, showed that different values of the Φ and Ψ torsion angles are observed already starting from the intermediates.

The present invention also relates to the analogues in which an amine is in the form of a tetraalkyl ammonium compound, which is a similar condition to that of amines at physiological pHs at which their activity is exerted.

In the definitions, $C_1$-$C_4$ alkyl group means a group selected from methyl, ethyl, n-propyl, isopropyl, n-butyl and t-butyl; $C_1$-$C_6$ alkyl group means a group selected from methyl, ethyl, n-propyl, isopropyl, n-butyl, n-pentyl, n-hexyl; cyclic aliphatic group having 3 to 7 carbon atoms means a group selected from cyclopropyl, cyclobutyl, cyclopentyl, cyclohexyl and cycloheptyl; aliphatic heterocyclic group having 3-7 atoms means a group selected from pyrrolidine optionally substituted at the N with a $C_1$-$C_4$ alkyl group, piperidine optionally substituted at the N with a $C_1$-$C_4$ alkyl group, tetrahydrofuran, tetrahydropyran, tetrahydrothiopyran; 5-7 membered aliphatic heterocyclic group means a group selected from pyrrolidine, piperidine, piperazine, morpholine, thiomorpholine, azepine, diazepine, oxazepine.

More particularly, the present invention relates to the compounds of general formula (I) in which:

$R_1$ is a hydrogen atom or a $C_1$-$C_4$ alkyl group;

$R_2$ and $R_3$, which can be the same or different, are a $C_1$-$C_4$ alkyl group, or $R_2$ and $R_3$, together with the carbon atom which they are linked to, form a cyclic aliphatic group having 3 to 7 carbon atoms or a heterocyclic aliphatic group having 3 to 7 atoms one or two of which are selected from the group of N, O, S and the other being C atoms;

$R_4$ and $R_5$, which can be the same or different, are a hydrogen atom or a $C_1$-$C_4$ alkyl group;

X is selected from the group consisting of halogen, $OR_1$, $SR_1$, CN, $C_1$-$C_4$ alkyl;

B has at least one amino group with basic characteristics or a tetraalkylammonium and can be selected from the group consisting of:

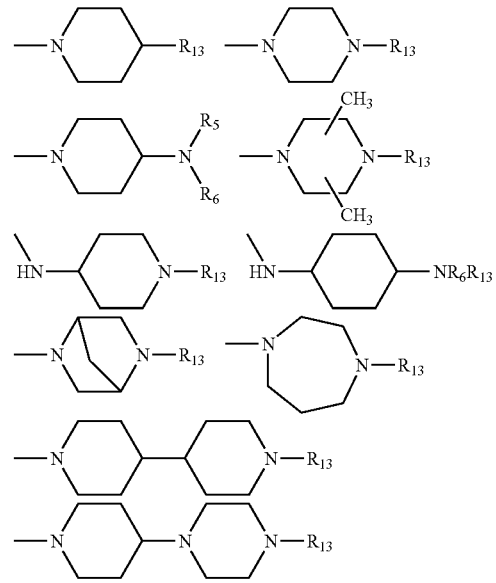

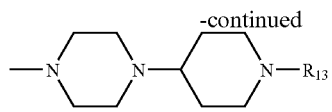

$R_6$ is a hydrogen atom, $C_1$-$C_6$ alkyl;

Y is selected from: hydrogen, $(CH_2)_pY_1$, $(CH_2)_pNR_6Y_1$, $(CH_2)_pN(Y_1)_2$, $NR_5R_6$, —$NR_6(CH_2)_pY_1$ or from the following residues:

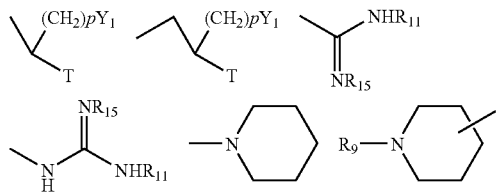

T is selected from the group of —$NR_7R_8$, —$NR_{14}R_{18}R_{19}$, —$OR_6$;

$R_7$ and $R_8$, which can be the same or different, are a hydrogen atom, a $C_1$-$C_4$ alkyl group, or $NR_7R_8$ is a group selected from: i) guanidine optionally substituted with 1 or 2 $C_1$-$C_4$ alkyl groups, cyclohexyl, ii) a 5-7 membered nitrogen heterocycle optionally containing another heteroatom selected from O, N, S;

$Y_1$ is selected from the group consisting of $NR_7R_8$, $NR_{14}R_{18}R_{19}$ or from the following residues:

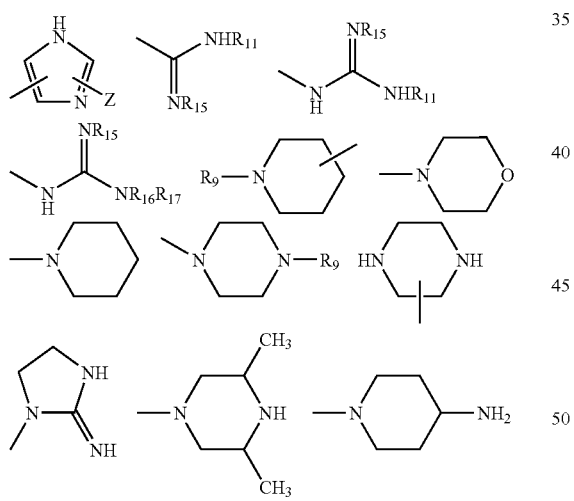

Z is selected from the group consisting of H, $C_1$-$C_6$ alkyl, $OR_6$, $SR_6$, $CF_3$, $OCOR_6$, $COR_{10}$, $NHCOR_6$, $SO_2R_6$, $SOR_6$, $CO_2R_6$, $N(R_6)_2$, Cl, Br, $NO_2$, $NH_2$, CN, F, imidazole, phenyl, amidine, guanidine, guanidyl-methyl;

$R_9$ is selected from the group consisting of hydrogen, —$(CH_2)_q$-L, wherein L is selected from the —OH group, —$NR_5R_6$, —$NR_{14}R_{18}R_{19}$, amidine optionally substituted with 1 or 2 $C_1$-$C_4$ alkyl groups, guanidine optionally substituted with 1 or 2 $C_1$-$C_4$ alkyl groups;

$R_{10}$ is selected from the group consisting of $OR_6$, $NR_6R_{12}$;

$R_{11}$ is selected from the group consisting of hydrogen, —$(CH_2)_q$-L, —$(CH_2)_p$—$NR_4$—$(CH_2)_q$-L;

$R_{12}$ is a hydrogen atom, $C_1$-$C_6$ alkyl, $COR_6$;

$R_{13}$ is selected from the group consisting of H, $C_1$-$C_6$ alkyl, —$(CH_2)_pW(CH_2)_qY_1$, Y, —COY, —$CH_2$—Y;

$R_{14}$ is selected from the group consisting of straight or branched $C_1$-$C_4$ alkyl groups;

R15 is selected from the group consisting of hydrogen or straight or branched $C_1$-$C_4$ alkyl groups;

the —$NR_{16}R_{17}$ group is a 5-7 membered nitrogen aliphatic heterocycle optionally containing another heteroatom selected from O, S, N;

the —$NR_{14}R_{18}R_{19}$ group is a quaternary ammonium group in which: $R_{14}$ is selected from the group consisting of straight or branched $C_1$-$C_4$ alkyl groups, $R_{18}$ and $R_{19}$, which can be the same or different, are a straight or branched $C_1$-$C_4$ alkyl group, or —$NR_{18}R_{19}$ is a 5-7 membered nitrogen heterocycle optionally containing another heteroatom selected from O, N, S;

W=$CH_2$, O, S, $NR_4$, $N(R_4)_2$;

p=1-6, q=1-6.

A class of preferred compounds are the compounds of general formula (I), in which:

B is selected from the group consisting of the residues:

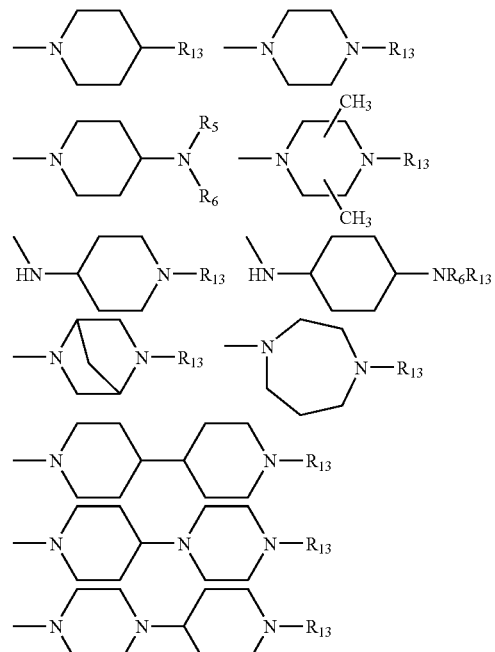

Y is selected from: $(CH_2)_pY_1$, $(CH_2)_pNR_6Y_1$, $(CH_2)_pN(Y_1)_2$, $NR_5R_6$, or from the following residues:

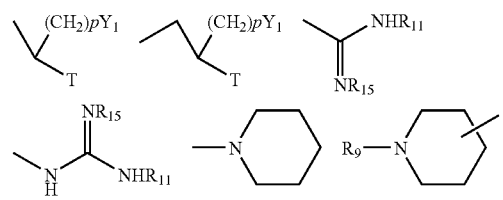

in which T is selected from the group of —$NR_7R_8$, —$OR_6$ and the other substituents are as defined above.

A particularly preferred class of compounds are the compounds in which:

$R_1$ is a hydrogen atom or methyl;
$R_2$ and $R_3$, which can be the same or different, are selected from methyl or ethyl, or $R_2$ and $R_3$, together with the carbon atom which they are linked to, form a cyclic aliphatic group having 3 to 7 carbon atoms;
$R_4$ and $R_5$, which can be the same or different, are a hydrogen or a methyl;
X is a chlorine atom;
B is a group selected from:

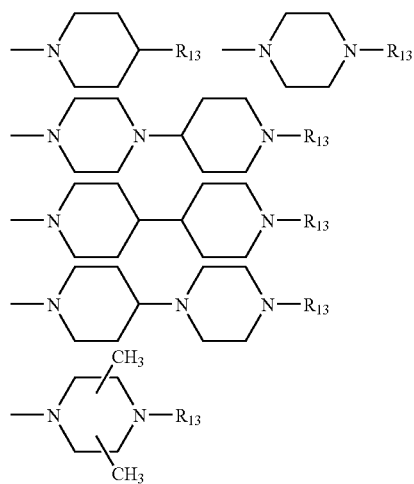

in which $R_{13}$ is H, or a $Y=Y_1$ group in which $Y_1$ is

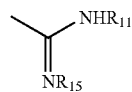

$R_{11}$ is selected from the group consisting of hydrogen, $—(CH_2)_q$-L, $—(CH_2)_p—NR_4—(CH_2)_q$-L wherein L is selected from —OH, —$NR_5R_6$, amidine optionally substituted with 1 or 2 $C_1$-$C_4$ alkyl groups, guanidine optionally substituted with 1 or 2 $C_1$-$C_4$ alkyl groups;

and the other substituents are as defined above.

A further class of particularly preferred compounds of general formula (I) are those in which:

$R_2$ and $R_3$, which can be the same or different, are selected from methyl or ethyl, or $R_2$ and R3, together with the carbon atom which they are linked to, form a cyclic aliphatic group having 3 to 7 carbon atoms;
$R_4$ and $R_5$, which can be the same or different, are a hydrogen or a methyl;
X is a chlorine atom;
B contains at least two amino groups with basic characteristics, in the free or salified form, and is selected from the group of:

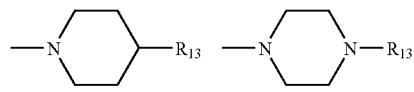

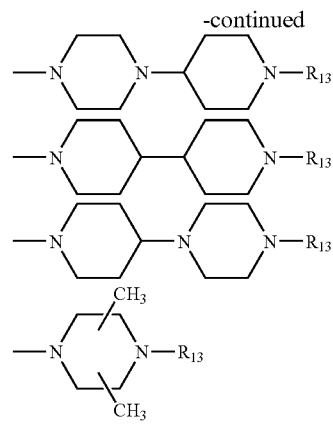

in which $R_{13}$ is COY, $CH_2Y$, $—(CH_2)_pW(CH_2)_qY_1$,
Y is a group $(CH_2)pY_1$, or is selected from:

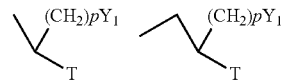

wherein T is selected from $—NR_7R_8$, $—OR_6$;
$R_7$ and $R_8$, which can be can be the same or different, are a hydrogen atom, a $C_1$-$C_4$ alkyl group, or $NR_7R_8$ is a group selected from: i) guanidine optionally substituted with 1 or 2 $C_1$-$C_4$ alkyl groups, cyclohexyl, ii) a 5-7 membered nitrogen heterocycle optionally containing another heteroatom selected from O, N, S;
$Y_1$ is selected from the group consisting of $—NR_7R_8$ and from the residues

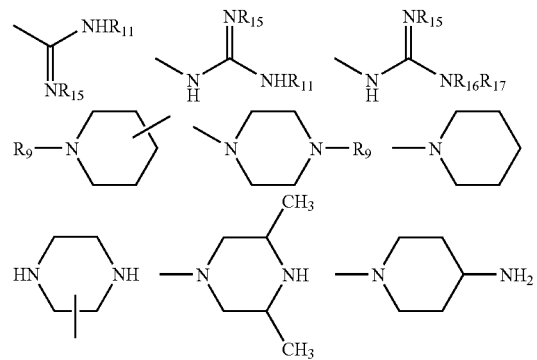

$R_9$ is selected from the group consisting of hydrogen, $—(CH_2)_q$-L, wherein L is selected from the group $—NR_5R_6$, amidine optionally substituted with 1 or 2 $C_1$-$C_4$ alkyl groups, guanidine optionally substituted with 1 or 2 $C_1$-$C_4$ alkyl groups; and the other substituents are as defined above.

A second class of preferred compounds of general formula (I), containing at least one tetralkylammonium, are those in which:

$R_1$ is a hydrogen atom or methyl;
$R_2$ and $R_3$, which can be the same or different, are selected from methyl or ethyl, or $R_2$ and R3, together with the carbon atom which they are linked to, form a cyclic aliphatic group having 3 to 7 carbon atoms;

$R_4$ and $R_5$, which can be the same or different, are a hydrogen or a methyl;

X is a chlorine atom;

B is selected from the group consisting of $NR_6Y$, and from the residues:

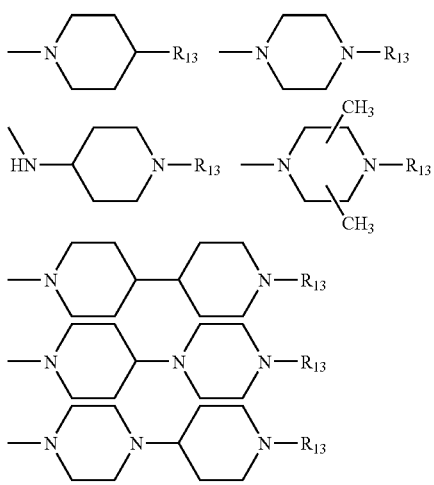

Y is selected from: Y, COY, $(CH_2)_pY_1$, $NR_6(CH_2)_qY_1$ and from the residues:

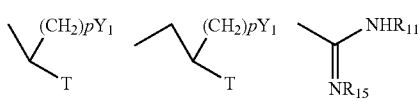

T is selected from the group $—NR_7R_8$, $—NR_{14}R_{18}R_{19}$, $—OR_6$;

$Y_1$ is selected from the group consisting of $—NR_7R_8$, $—NR_7R_8R_{14}$ or from the following residues:

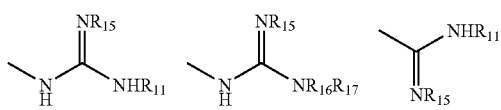

and the other substituents are as defined above.

The compounds of general formula (I) can be prepared according to well known synthetic routes.

By way of example, and particularly interesting for the purposes of the invention, the compounds of general formula (I) as defined above in which B is the group

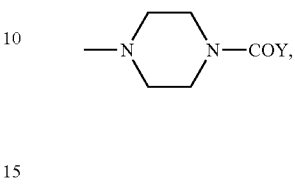

can be prepared by condensation, in the presence of a suitable condensing agent, of the intermediate of general formula (II)

(II)

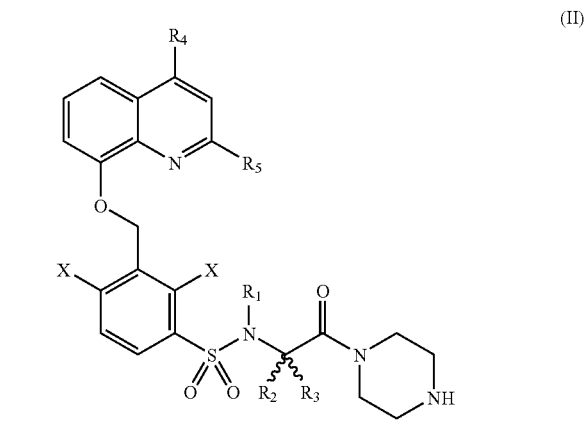

with an acylating group, such as 2,6-diaminohexanoic acid, which is commercially available. Compound (1)(intermediate of general formula (II) in which $R_1$=H) can be prepared according to the scheme reported in the following.

Scheme 1

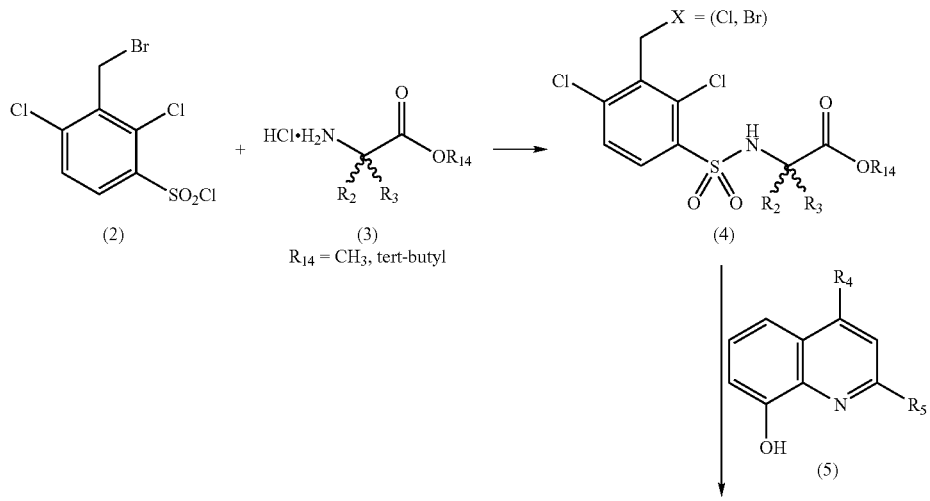

-continued

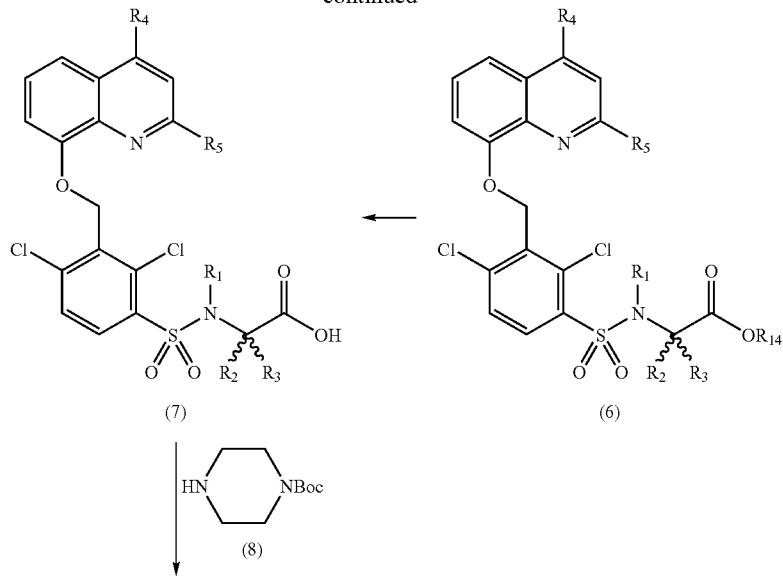

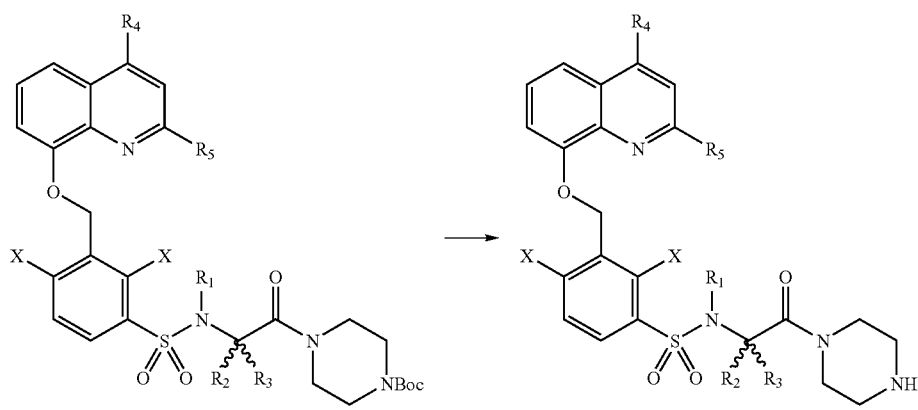

Compound (1) is obtained through a series of reactions shown in Scheme 1. The first step relates consists in the formation of the sulfonamido bond (4) obtained by condensation of intermediates (2) and (3). This reaction is carried out at room temperature, preferably in acetonitrile/water (2:1), in the presence of NaHCO$_3$. Said reaction takes place with chlorine—bromine exchange on the benzyl position: the resulting products mixture is used as such as for the subsequent step. The halogen derivatives mixture is then reacted with a disubstituted hydroxyquinoline (5), in the presence of potassium carbonate (K$_2$CO$_3$) and potassium iodide (KI), in acetone under reflux, to obtain the ether derivative (6). The methyl ester of formula (6) in which R$_{14}$=CH$_3$, is hydrolysed in basic conditions to carboxylic acid (7), which is then condensed with Boc-piperazine (8), to afford intermediate (9). Said condensation reaction is carried out according to a procedure known in the peptide synthesis, using hydroxybenzotriazole to activate the carboxylic component, a condensing agent such as 1-ethyl-3-(3'-dimethylpropyl)carbodiimide and an amount of tertiary amine, diisopropylethylamine, corresponding to three equivalents compared with the condensing agent. Finally, compound (1) is obtained by cleaving the Boc group from intermediate (9), with a hydrochloric acid solution (4N) in dioxane and isolating the free amine instead of the hydrochloride.

Compound of formula (2) is prepared as described in J. Fluorine Chemistry, 2000, 101:85-89.

Compound of formula (5), i.e. 2,4-dimethyl-8-hydroxyquinoline (R$_4$=R$_5$=CH$_3$), is prepared as disclosed in WO9640639.

In case R$_1$ is an alkyl group, in particular methyl, alkylation of the sulfonamido group of compound (6) is carried out; by way of example, the preparation of intermediate (7) in which R$_1$=methyl, is shown in scheme 2.

Scheme 2

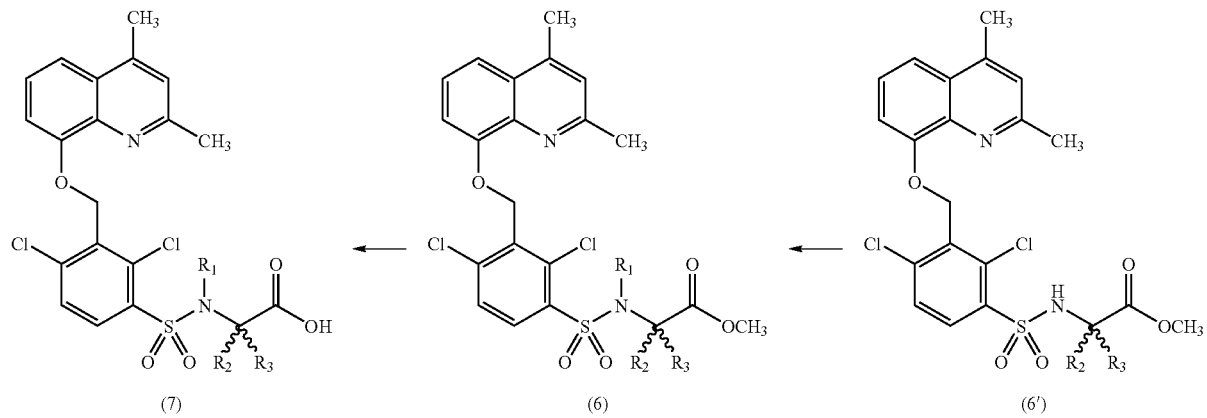

(7) ← (6) ← (6')

The sulfonamido nitrogen can be alkylated in dimethylformamide using methyl iodide as alkylating agent and potassium carbonate ($K_2CO_3$) as base.

All compounds of general formula (I) can be obtained suitably changing the procedure of scheme 2, by means of conventional acylation or alkylation reactions on the nitrogen atom in intermediates such as compound (1) or the analogues thereof.

The intermediates and final products of the present invention are recovered and purified through conventional procedures, such as extraction, crystallization, chromatography, precipitation and the like.

In case intermediates and final products have an asymmetric carbon atom, when the configuration (R,S) is not specified, the compounds are racemic compounds or racemates.

In the present invention, the following abbreviations are used: DCM=dichloromethane; MeOH=methanol; THF=tetrahydrofuran; DMSO=dimethylsulfoxide; DMF=dimethylformamide; AcOEt=ethyl acetate; AcOH=acetic acid; TFA=trifluoroacetic acid; pTsOH=para-toluenesulfonic acid; PPA=poliphosphoric acid; NBS=$N_\alpha$-bromosuccinimide; bpo=benzoyl peroxide; Boc=tert-butoxycarbonyl; HOBt=1-hydroxy-benzotriazole; HOAt=1-hydroxy-7-aza-benzotriazole; EDC=1-ethyl-3-(3'-dimethylpropyl)carbodiimide; DIPEA=diisopropylethylamine; TLC=thin-layer chromatography; NMR=nuclear magnetic resonance; FCC=Flash Column Chromatography; $t_R$=retention time.

The intermediates and final products of the present invention were characterized by analytic HPLC: column Symmetry 300, C18, 5 μm, 250×4.6 mm, using A (0.1% TFA in $H_2O$) and B (0.1% TFA in acetonitrile) as eluents, with a gradient of 20 to 80% B in 20 minutes, λ=220 nm. For the compounds characterized through nuclear magnetic resonance (NMR), the values of proton chemical shifts are reported, as well as the signal multiplicity and the number of protons (in brackets).

The compounds of the invention are used in the treatment of all those disorders in which the activation of bradykinin receptor has to be blocked or reduced. They are particularly suitable for the treatment of inflammatory, allergic and autoimmune disorders, such as asthma and chronic bronchitis, allergic, vasomotor and viral rhinitis, obstructive pulmonary disease (COPD), rheumatoid arthritis, chronic inflammatory diseases of the bowel (Crohn's disease and ulcerative colitis), glomerulonephritis, psoriasis, rash, acute and chronic cystitis, hepatic cirrhosis, glomerulopathies and pulmonary fibrosis, arteriosclerosis, both acute and chronic pain, septic, allergic and post-traumatic shocks, hepatic cirrhosis by hepatorenal syndrome, hypotension, alopecia, or as anticancer and antiangiogenetics.

For use in therapy, the compounds of the invention will be suitably formulated together with pharmaceutically acceptable carriers/excipients. Preferred are pharmaceutical forms suitable for the oral administration, such as tablets, capsules, granules, powders, solutions, suspensions, syrups or the like. These pharmaceutical preparations can be prepared with conventional procedures using ingredients known in technique, such as ligands, disintegrants, lubricants, fillers, stabilizing agents, diluents, dyes, flavours, wetting agents and other excipients known to those skilled in the art. The oral formulations also comprise protracted-release forms, such as enteric-coated tablets or granules. The solid oral compositions can be prepared with conventional mixing, filling or compression methods. The liquid oral preparations can be in the form of, for example, aqueous or oily suspensions or solutions, emulsions, syrups, or can be presented as dry product for reconstitution with water or other suitable carrier before use.

The dosage can range depending on the age and general conditions of the patient, nature and severity of the disease or disorder and route and type of administration. As a rule, in case of oral administration to a human adult patient, the compounds of the present invention will be generally administered at a total ranging daily dosage from 1 to 1000-mg, preferably from 5 to 300 mg, in a single dose or in subdivided doses.

The following examples illustrate the invention in greater detail.

EXAMPLE 1

(Intermediate of Formula (4) in which $R_2$=$CH_3$, $R_3$=$CH_2CH_3$, $R_{14}$=$CH_3$) Methyl (R)-2-(2,4-dichloro-3-bromomethyl-benzenesulfonamido)-2-methyl methylbutanoate A solution of (R)-methyl 2-(methylamino)-2-methylbutanoate (30 mg, 0.18 mmol) in DMF (2ml) is added with 69 μl (0.40 mmol) of DIEA; then with 125 mg (0.369 mmol) of 2,4-dichloro-3-bromomethyl-benzensulfonyl chloride (2) at 0° C. The system is left to warm at room temperature; after reacting for approx. 30 minutes, the solution pH changes from basic to strongly acid. The reaction is monitored by TLC: disappearance of the spot of 2,4-dichloro-3-bromomethyl-benzensulfonyl chloride and formation of the final product are observed. DMF is evaporated off under reduced pressure and the reaction crude is purified on chromatographic column (FCC) eluted with 100% chloroform, thereby obtaining 49 mg of product as a colourless oil, in a 63% yield.

HPLC: $t_R$=21.84 min; MS: $[M+NH_4]^+$=449.0; $^1H$ NMR ($CDCl_3$): 8.00 (d, 1H, J=9.0 Hz); 7.46 (d, 1H, J=9.0 Hz); 4.90 (s, 2H); 3.70 (s, 3H); 2.01-1.88 (m, 1H); 1.82-1.68 (m, 1H); 1.36 (s, 3H); 0.74 (t, 3H, J=8.4 Hz).

EXAMPLE 2

(Intermediate of Formula (6) in which $R_4$=$R_5$=$CH_3$, $R_2$=$CH_3$, $R_3$=$CH_2CH_3$, $R_{14}$=$CH_3$) Methyl (R)-2-[2,4-dichloro-3-(2,4-dimethyl-8-quinolinoxymethyl)-benzene-sulfonamido]-2-methylbutanoate A solution of the products obtained as described in example 1 (49 mg, 0.283 mmol), in anhydrous acetone (10 ml) is added with 110 mg (0.283 mmol) of 2,4-dimethyl-8-hydroxyquinoline, 58 mg of KI (0.349 mmol) previously dried over phosphoric anhydride at 75° C., and finally, 80 mg (0.579 mmol) of $K_2CO_3$. The solution is refluxed for about five hours and a half, until complete disappearance (monitored by HPLC) of the starting products. After cooling at room temperature, the is partitioned between AcOEt (50 ml) and a buffer solution at pH=4 (90 ml). The organic phase is separated and washed with the buffer solution (50 ml); the aqueous phases are combined, and back-extracted with about 50 ml of AcOEt. Finally, the organic phase is washed with water and brine, dried over sodium sulfate, filtered and evaporated to dryness; the crude product is purified by FCC eluting with hexane/AcOEt (2:1), to give 79 mg (yield: 53%) of methyl (R)-2-[2,4-dichloro-3-(2,4-dimethyl-8-quinolinoxymethyl)benzenesulfonamido]-2-methylbutanoate, as a pale yellow oil.

HPLC: $t_R$=16.19 min; MS: $[M+H]^+$=525.1; $^1H$ NMR $CDCl_3$): 8.02 (d, 1H, J=8.6 Hz); 7.60 (d, 1H, J=8.4 Hz); 7.47 (d, 1H, J=8.6 Hz); 7.36 (t, 1H, J=8.0 Hz); 7.21 (t, 1H, J=7.6 Hz); 7.11 (s, 1H); 6.00 (s, 1H); 5.66 (dd, 2H, $J_1$=14.8 Hz, $J_2$=10.7 Hz); 2.64 (s, 3H); 2.62 (s, 3H); 2.05-1.90 (m, 1H, J=42.3 Hz); 1.83-1.71(m, 1H, J=28.7 Hz); 1.47 (s, 3H); 0.78 (t, 3H, J=7.4 Hz).

The compounds of the examples reported in the following were prepared analogously.

EXAMPLE 3

(Intermediate of Formula (6) in which $R_4$=$R_5$=$CH_3$, $R_2$=$CH_3$, $R_3$=$CH_2CH_3$, $R_{14}$=$CH_3$) Methyl (S)-2-[2,4-dichloro-3-(2,4-dimethyl-8-quinolinoxymethyl)-benzene-sulfonamido]-2-methylbutanoate HPLC: $t_R$=16.19 min; MS: $[M+H]^+$=525.0; $^1H$ NMR ($CDCl_3$): 8.01 (d, 1H, J=8.6 Hz); 7.60 (d, 1H, J=8.4 Hz); 7.47 (d, 1H, J=8.6 Hz); 7.37 (t, 1H, J=7.8 Hz); 7.12 (t, 1H, J=7.6 Hz); 6.00 (s, 1H); 5.65 (dd, 2H, $J_1$=14.8 Hz, $J_2$=10.7 Hz); 3.69 (s, 3H); 2.65 (s, 3H); 2.10-1.89 (m, 1H); 1.83-1.69 (m, 1H); 1.37 (s, 3H); 0.78 (t, 3H, J=7.4 Hz).

EXAMPLE 4

(Intermediate of Formula (6) in which $R_4$=$R_5$=$CH_3$, $R_2$=$R_3$=$CH_3$, $R_{14}$=$C(CH_3)_3$) tert-Butyl 2-[2,4-dichloro-3-(2,4-dimethyl-8-quinolinoxymethyl)-benzene-sulfonamido]-2-methylpropanoate HPLC: $t_R$=14.27 min; MS: $[M+H]^+$=553.1; $^1H$ NMR ($CDCl_3$):8.05 (d, 1H, J=8.6 Hz); 7.61 (d, 1H, J=8.4 Hz); 7.47 (d, 1H, J=8.6 Hz); 7.38 (t, 1H, J=7.9 Hz); 7.21 (d, 1H, J=7.6 Hz); 7.13 (s, 1H); 6.09 (s, 1H); 5.67 (s, 2H); 2.67 (s, 3H); 2.63 (s, 3H); 1.45 (s, 9H); 1.40 (s, 6H).

EXAMPLE 5

(Intermediate of Formula (6) in which $R_4$=H, $R_5$=$CH_3$, $R_2$=$CH_3$, $R_3$=$CH_2CH_3$, $R_{14}$=$C(CH_3)_3$) tert-Butyl 2-[2,4-dichloro-3-(2-methyl-8-quinolinoxymethyl)-benzene-sulfonamido]-2-methylpropanoate MS: $[M+H]^+$=539.0; $^1H$ NMR ($CDCl_3$): 8.08 (d, 1H, J=8.6 Hz); 8.03 (d, 1H, J=8.4 Hz); 7.51 (d, 1H, J=8.6 Hz); 7.46 (d, 1H, J=7.1 Hz); 7.39 (t, 1H, J=7.6 Hz); 7.35-7.23 (m, 2H); 6.12 (s, 1H); 5.71 (s, 2H); 2.75 (s, 3H); 1.48 (s, 9H); 1.43 (s, 6H).

EXAMPLE 6

(Intermediate of Formula (6) in which $R_4$=$R_5$=$CH_3$, $R_2$ and $R_3$, Together with the Carbon Atom which they are Linked to, from a Cyclopentyl, $R_{14}$=$CH_3$) Methyl 1-[2,4-dichloro-3-(2,4-dimethyl-8-quinolinoxymethyl)]benzene-sulfonamido-1-cyclopentanecarboxylate HPLC: $t_R$=11.16 min; MS: $[M+H]^+$=537.0; $^1H$ NMR (DMSO): 8.64 (s, 1H), 8.03 (d, 1H, J=8.6 Hz); 7.79-7.29 (m, 5H); 5.59 (s, 2H); 3.56 (s, 3H); 2.89-2.57 (m, 6H); 1.98-1.85 (m, 4H); 1.60-1.48 (m, 2H); 1.48-1.38 (m, 2H).

EXAMPLE 7

(Intermediate of Formula (6) in which $R_4$=H, $R_5$=$CH_3$, $R_2$ and R3, Together with the Carbon Atom which they are Linked to, form a Cyclopentyl, $R_{14}$=$CH_3$) Methyl 1-[2,4-dichloro-3-(2-methyl-8-quinolinoxymethyl)]benzene-sulfonamido-1-cyclopentanecarboxylate HPLC: $t_R$=15.43 min; MS: $[M+H]^+$=523.2; $^1H$ NMR ($CDCl_3$): 8.07-8.01 (m, 2H, J1=1.6 Hz, J2=8.6 Hz); 7.54 (d, 1H, J=8.6 Hz); 7.49-7.38 (m, 2H); 7.31 (d, 1H, J=8.4 Hz); 7.25 (dd, 1H, $J_1$=7.5 Hz; $J_2$=1.2 Hz); 5.70 (s, 2H); 5.48 (s, 1H); 3.66 (s, 3H); 2.73 (s, 3H); 2.21-2.10 (m, 2H); 2.01-1.91 (m, 2H); 1.75-1.65 (m, 4H).

EXAMPLE 8

(Intermediate of Formula (6') in which $R_1$=$CH_3$, $R_2$ and $R_3$, Together with the Carbon Atom which they are Linked to, from a Cyclopentane) Methyl 1-[2,4-dichloro-3-(2,4-dimethyl-8-quinolinoxymethyl)]-1-N'-methyl-benzenesulfonamido-1-cyclopentanecarboxylate A solution of methyl 1-[2,4-dichloro-3-(2,4-dimethyl-8-quinolinoxymethyl)]benzenesulfonamido-1-cyclopentanecarboxylate (50 mg, 0.093 mmol) in 5 ml of DMF is added with $CH_3I$ (19.2 ml, 0.306 mmol) and 29 mg of $K_2CO_3$ (0.186 mmol), at 0° C. under nitrogen atmosphere. After stirring at room temperature for about 3 hours, the reaction mixture is poured in 50 ml of buffer solution pH=4.2, then extracted with AcOEt (3×30 ml). The organic phase is subsequently washed with water and brine, dried over sodium sulfate, filtered and evaporated under reduced pressure to obtain 52 mg (0.093 mmol) of desired product as a brown solid, in a quantitative yield.

HPLC: $t_R$=13.56 min; MS: $[M+H]^+$=551.4; $^1H$ NMR ($CDCl_3$): 8.07 (d, 1H, J=8.6 Hz); 7.64 (d, 1H, J=8.6 Hz); 7.17 (s, 1H); 5.69 (s, 2H); 3.78 (s, 3H); 3.35 (s, 3H); 2.72 (d, 6H, J=44.9 Hz); 2.24 (m, 2H); 1.93 (m, 2H); 1.63 (m, 4H).

EXAMPLE 9

(Intermediate of Formula (7) in which $R_4$=$R_5$=$CH_3$, $R_2$=$R_3$=$CH_3$, $R_3$=$CH_2CH_3$) Lithium (R)-2-[2,4-dichloro-3-(2,4-dimethyl-8-quinolinoxymethyl)-benzene-sulfonamido]-2-methylbutanoate A solution of the product described in example 4 (79 mg, 0.15 mmol) in THF/MeOH/$H_2O$ (3:2:1, 6 ml) is added with 23 mg (0.96 mmol) of LiOH. The reaction is stirred at room temperature for about 18 hours, then temperature is raised to 45° C. for about 27 hours, to promote the hydrolysis reaction. THF and MeOH are then evaporated off under reduced pressure, and the alkaline solution is partitioned between AcOEt (25 ml) and water (25 ml). NaCl is added to break the resulting emulsion, the two phases are separated, the aqueous phase is acidified to pH=4 with 4N HCl, then extracted with AcOEt (25 ml). The organic phase is then washed with brine, dried over sodium sulfate, filtered and dried to afford 64 mg of product as a yellow solid, in an 82% yield.

HPLC: $t_R$=14.36 min; MS: $[M+H]^+$=511.0; $^1H$ NMR (DMSO): 8.09 (s, 1H); 8.06 (d, 1H, J=8.6 Hz); 7.73 (d, 1H, J=8.6 Hz); 7.64 (d, 1H, J=8.3 Hz); 7.46 (t, 1H, J=7.9 Hz); 7.34 (d, 1H, J=7.6 Hz); 7.27 (s, 1H), 5.51 (dd, 2H, J1=13.8 Hz, $J_2$=10.8 Hz); 2.61 (s, 3H); 2.54 (s, 3H); 1.62 (dd, 2H, $J_1$=14.4 Hz, $J_2$=7.1 Hz); 1.01 (s, 3H); 0.61 (t, 3H, J=7.1 Hz).

The compounds of the examples reported in the following were prepared analogously.

EXAMPLE 10

(Intermediate of Formula (7) in which $R_4$=$R_5$=$CH_3$, $R_2$=$R_3$=$CH_3$, $R_3$=$CH_2CH_3$) Lithium (S)-2-[2,4-dichloro-3-(2,4-dimethyl-8-quinolinoxymethyl)-benzene-sulfonamido]-2-methylbutanoate HPLC: $t_R$=14.24 min; $^1H$ NMR ($CDCl_3$): 8.09 (d, 1H, J=8.6 Hz); 7.62-7.47 (m, 3H, J=48.5 Hz); 7.15 (s, 1H); 5.62 (d, 1H, J=9.6 Hz); 5.56 (s, 1H); 5.47 (d, 1H, J=9.6 Hz); 2.66 (s, 3H); 2.53 (s, 3H); 1.86-1.64 (m, 2H, J=58.6 Hz); 1.37 (s, 3H); 0.95 (t, 3H, J=7.4 Hz).

EXAMPLE 11

(Intermediate of Formula (7) in which $R_4$=$R_5$=$CH_3$, $R_2$=$R_3$=$CH_3$) 2-[2,4-Dichloro-3-(2,4-dimethyl-8-quinolinoxymethyl)benzenesulfonamido]-2-methylpropionic acid HPLC: $t_R$=9.09 min; MS: $[M+H]^+$=497.0.

EXAMPLE 12

(Intermediate of Formula (7) in which $R_4$=H, $R_5$=$CH_3$, $R_2$=$R_3$=$CH_3$) 2-[2,4-Dichloro-3-(2-methyl-8-quinolinoxymethyl)benzenesulfonamido]-2-methylpropionic acid HPLC: $t_R$=8.34 min; MS: $[M+H]^+$=483.0, $^1H$ NMR ($CDCl_3$): 8.68 (d, 1H, J=8.6 Hz); 8.17 (d, 1H, J=8.7 Hz); 7.83 (t, 1H, J=8.1 Hz); 7.63 (d, 1H, J=8.7); 7.75-7.66 (m, 2H); 5.66 (s, 2H); 5.50 (s, 1H); 2.94 (s, 3H); 1.52 (s, 6H).

EXAMPLE 13

(Intermediate of Formula (7) in which $R_4$=$R_5$=$CH_3$, $R_2$ and $R_3$, Together with the Carbon Atom which they are Linked to, form a Cyclopentyl) 1-[2,4-Dichloro-3-(2,4-dimethyl-8-quinolinoxymethyl)]benzene-sulfonamido-1-cyclopentanecarboxylic acid HPLC: $t_R$=9.969 min; MS: $[M+H]^+$=523.0

EXAMPLE 14

(Intermediate of Formula (7) in which $R_4$=H, $R_5$=$CH_3$, $R_2$ and R3, Together with the Carbon Atom which they are Linked to, form a Cyclopentyl) 1-[2,4-Dichloro-3-(2-methyl-8-quinolinoxymethyl)]benzenesulfonamido-1-cyclopentanecarboxylic acid HPLC: eq.: $t_R$=13.18 min(42.6%)-$t_R$=13.35 min(49.4%); MS: $[M]^-$=507.0; $^1H$ NMR (DMSO): 12.57 (br s, 1H); 8.45 (s, 1H); 8.20 (d, 1H, J=8.4 Hz); 7.76 (d, 1H, J=8.6 Hz); 7.33-7.58 (m, 4H, J=77.1 Hz); 5.53 (s, 2H); 2.59 (s, 3H); 1.94-1.84 (m, 4H, J=42.3 Hz); 1.60-1.30 (m, 4H, J=92.8 Hz).

EXAMPLE 15

Intermediate 4-{1-[2,4-Dichloro-3-(2,4-dimethyl-quinolin-8-yloxymethyl)-benzenesulfonylamino]-cyclopentanecarbonyl}-piperazine-1-carboxylic acid tert-butyl ester A solution in DMF (2 ml) of the product described in example 15 (0.12 mmol), is added with 22 mg (0.16 mmol) of HOAt and 29 mg (0.15 mmol) of EDC.HCl. The mixture is stirred at 0° C. for about 30 min, then added with 32 mg (0.18 mmol) of tert-butyl-N-(piperazinyl)carbamate diluted in 2 ml of DMF. The mixture is left to warm at room temperature under stirring for 4 hours. The solvent is evaporated off and the product is purified by preparative chromatography using a column Simmetry Prep™ filled with RP-18 10 μm, eluting with a gradient of 90% water in acetonitrile to 50% water in acetonitrile during 40 minutes with a 10 ml/min flow. The fractions corresponding to the desired product are combined and the solvent is evaporated off thereby obtaining 48 mg of the product as a colourless oil in a 58% yield.

HPLC: $t_R$=16.68 min; MS: [M+H]$^+$=691.5; $^1$H NMR (DMSO-d$_6$) δ: 8.57 (1H, s), 8.02 (1H, d), 7.80 (1H, d), 7.66 (1H, d), 7.48 (1H, t), 7.35 (1H, d), 7.29 (1H, s), 5.54 (2H, s), 2.62 (3H, s), 2.55 (3H, s), 2.04-1.89 (2H, m), 1.82-1.66 (4H, m), 1.41 (9H, s).

EXAMPLE 16

2,4-Dichloro-3-(2,4-dimethyl-quinolin-8-yloxymethyl)-N-[1-(piperazine-1-carbonyl)-cyclopentyl]-benzenesulfonamide A solution of 4N HCl in dioxane (2 ml) is dropwise added, at room temperature, to a methanol solution (4 ml) of the intermediate described in Example 15 (0.072 mmol). The mixture is kept under stirring for about an hour, then evaporated to dryness under reduced pressure; the residue is taken up into a MeOH/toluene solution, which is then evaporated to yield a white solid. The product is then washed with ethyl ether, filtered, partitioned between AcOEt (25 ml) and a 5% NaHCO$_3$ aqueous solution (25 ml); the two phases are separated and the organic phase is washed with 25 ml of a 5% NaHCO$_3$ aqueous solution. The combined aqueous phases are back-extracted with 25 ml of AcOEt, finally the combined organic phases are washed with brine, dried over sodium sulfate, filtered and evaporated, thereby obtaining 25 mg a colourless oil in a 66% yield.

HPLC: $t_R$=8.34 min; MS: [M+H]$^+$=591.2; $^1$H NMR (DMSO-d$_6$): 8.83 (brs, 2H); 8.64 (s, 1H); 8.02 (d, 1H); 7.82 (d, 1H); 7.6-7.4 (m, 4H); . 5.58 (s, 2H); 3.4-2.6 (6H); 1.98 (m, 2H); 1.72 (m, 2H); 1.43 (s, 4H).

EXAMPLE 17

2,4-Dichloro-N-(1,1-dimethyl-2-oxo-2-piperazin-1-yl-ethyl)-3-(2-methyl-quinolin-8-yloxymethyl)-benzenesulfonamide HPLC: $t_R$=5.98 min; MS: [M+H]$^+$=551.1; $^1$H NMR (DMSO-d$_6$): 8.85 (brs, 2H); 8.72 (s, 1H); 8.33 (brs, 1H); 8.07 (d, 1H); 7.82 (d, 1H); 7.63-7.40 (m, 4H); 5.58 (s, 2H); 3.17 (m, 4H); 2.66 (s, 3H); 1.23 (s, 6H).

EXAMPLE 18

N-[2-[4-(2-(S)-Amino-6-dimethylaminohexanoyl)-piperazin-1-yl]-1,1-dimethyl-2-oxo-ethyl]-2,4-dichloro-3-(2-methyl-quinolin-8-yloxymethyl)-benzenesulfonamide trifluoroacetate A solution of 2,6-bis-tert-butyloxycarbonylamino-hexanoic acid (0.060 mmol) and HOAt (11 mg, 0.081 mmol) in DMF (1 ml), cooled at 0° C., is added with EDC.HCl (17 mg, 0.089 mmol) in a single portion. After stirring for 30 minutes, the compound described in example 17 (21 mg, 0.037 mmol) dissolved in 2 ml of DMF is added at 0° C. and the mixture is kept at this temperature for a further 30 minutes, then left to warm at room temperature.

After approx. 18 hours, stirring is discontinued and DMF is removed under reduced pressure. The resulting residue is dissolved in 3 ml of a 0.1% TFA aqueous solution and filtered through Anotop 25. The resulting aqueous solution is subjected to preparative chromatography eluting with a gradient of 90% water in acetonitrile to 50% water in acetonitrile during 40 minutes, with a 10 ml/min flow. The fractions containing the product are recovered and combined and the solvent is evaporated off, to obtain 20 mg of product as a colourless oil. The oil is triturated in ethyl ether (3 ml) and filtered under nitrogen. The resulting solid is washed with ethyl ether and dried under nitrogen stream to afford 8.8 mg of white solid (yield 26%). The Boc groups are then removed as in Example 16.

$^1$H NMR (DMSO-d$_6$) δ: 9.38-9.26 (1H, brs), 8.72 (1H, s), 8.38-8.26 (1H, brs), 8.19-8.09 (3H, m), 8.07 (1H, d), 7.83 (1H, d), 7.64-7.39 (4H, m), 5.58 (1H, s), 4.52-4.42 (1H, m), 3.04-2.95 (2H, m), 2.80-2.73 (6H, m), 2.69-2.62 (5H, m), 1.77-1.54 (4H, m), 1.43-1.21 (8H, m).HPLC $t_R$=8.16 min; MS: [M+H]$^+$=707.2.

EXAMPLE 19

N-{2-[4-(6-Guanidinohexyl)-piperazin-1-yl]-1,1-dimethyl-2-oxo-ethyl}-2,4-dichloro-3-(2-methyl-8-quinolinoxymethyl)benzenesulfonamido-2-methyl-propionamide tris trifluoroacetate HPLC: $t_R$=6.46 min; MS: [M+H]$^+$=692.2.

$^1$H NMR (DMSO-d6) δ: 9.38-9.26 (1H, brs), 8.72 (1H, s), 8.38-8.26 (1H, brs), 8.19-8.09 (3H, m), 8.07 (1H, d), 7.83 (1H, d), 7.64-7.39 (4H, m), 5.58 (1H, s), 4.52-4.42 (1H, m), 3.04-2.95 (2H, m), 2.80-2.73 (6H, m), 2.69-2.62 (5H, m), 1.77-1.54 (4H, m), 1.43-1.21 (8H, m).

EXAMPLE 20

4-{2-[2,4-Dichloro-3-(2-methyl-quinolin-8-yloxymethyl)-benzenesulfonylamino]-2-methyl-propionyl}-piperazine-1-carboxamidine HPLC: $t_R$=6.34 min; MS: [M+H]$^+$=593.3; $^1$H NMR (DMSO-d$_6$): 8.71 (s, 1H); 8.06 (d, 1H); 7.82 (d, 1H); 7.6-7.4 (m, 5H,); 5.57 (s, 2H); 3.6-3.5 (m, 4H); 2.63 (s, 3H); 1.23 (s, 6H)

EXAMPLE 21

N-[2-[4-(2-(S)-Amino-5-guanidino-pentanoyl)-piperazin-1-yl]-1,1-dimethyl-2-oxo-ethyl]-2,4-dichloro-3-(2-methyl-8-quinolinoxymethyl)-benzenesulfonamide tris trifluoroacetate HPLC: $t_R$=7.62 min; MS: [M+H]$^+$=707.1. $^1$H NMR (DMSO-d$_6$) δ: 8.73 (1H, s), 8.42-8.32 (1H, brs), 8.26-8.16 (3H, brs), 8.07 (1H, d), 7.82 (1H, d), 7.66-7.00 (7H, m), 5.58 (1H, s), 3.19-3.09 (2H, m), 2.67(3H, s), 1.80-1.45 (4H, m), 1.30-1.21 (6H, m).

EXAMPLE 22

N-{2-[4-(6-Aminohexyl)-piperazin-1-yl]-1,1-dimethyl-2-oxo-ethyl}-2,4-dichloro-3-(2-methyl-8-quinolinoxymethyl)-benzenesulfonamide tris trifluoroacetate HPLC: $t_R$=6.02 min; MS: [M+H]$^+$=649.9. $^1$H NMR (DMSO-d$_6$) δ: 8.80 (1H, s), 8.08 (1H, d), 7.96-7.80 (3H, m), 7.83 (1H, d), 7.70-7.50 (3H, m), 5.60 (1H, s), 4.58 (2H, m), 3.12-3.03 (2H, m), 3.02-2.84 (1H, m), 2.81-2.69 (2H, m), 1.79 (2H, m), 1.60-1.50 (2H, m), 1.40-1.28 (4H, m), 1.25 (6H, s).

EXAMPLE 23

N-{2-[4-(Piperazin-2-yl)-piperazin-1-yl]-1,1-dimethyl-2-oxo-ethyl}-2,4-dichloro-3-(2-methyl-8-quinolinoxymethyl)-benzenesulfonamide tris trifluoroacetate HPLC: $t_R$=7.54 min; MS: [M+H]$^+$=663.0. $^1$H NMR (DMSO-d$_6$) δ: 8.69 (1H, s), 8.53-8.31 (2H, m), 8.24-8.02 (1H, m), 8.07 (1H, d), 7.81 (1H, d), 7.69-7.41 (4H, m), 5.59 (2H, s), 3.29-3.19 (2H, m), 2.96-2.81 (2H, m), 2.68 (3H, m), 2.39-2.31 (2H, m), 2.06-1.93 (1H, m), 1.89-1.79 (2H, m), 1.39-1.18 (9H, m).

EXAMPLE 24

N-{2-[4-(Piperazin-1-ylacetyl)-piperazin-1-yl]-1,1-dimethyl-2-oxo-ethyl]-2,4-dichloro-3-(2-methyl-8-quinolinoxymethyl)-benzenesulfonamide bis trifluoroacetate HPLC: $t_R$=7.67 min; MS: [M+H]$^+$=667.1. $^1$H NMR (DMSO-d$_6$) δ: 9.00-8.78 (1H, brs), 8.74 (1H, s), 8.44-8.21 (2H, brs), 8.07 (1H, d), 7.82 (1H, d), 7.67-7.40 (4H, m), 5.57 (1H, s), 3.66-3.45 (4H, m), 3.36-3.18 (3H, m), 3.12-2.98 (3H, m), 2.72-2.61 (3H, m), 1.70-1.60 (2H, m), 1.60-1.51 (1H, m), 1.30-1.21 (7H, m).

EXAMPLE 25

N-{2-[4-2-(Piperidin-4-yl-acetyl)-piperazin-1-yl]-1,1-dimethyl-2-oxo-ethyl}-2,4-dichloro-3-(2-methyl-8-quinolinoxymethyl)-benzenesulfonamide bis trifluoroacetate HPLC: $t_R$=8.32 min; MS: [M+H]$^+$=676.1; $^1$H NMR (DMSO-d$_6$) δ: 8.69 (1H, s), 8.53-8.31 (2H, m), 8.24-8.02 (1H, m), 8.07 (1H, d), 7.81 (1H, d), 7.69-7.41 (4H, m), 5.59 (2H, s), 3.29-3.19 (2H, m), 2.96-2.81 (2H, m), 2.68 (3H, m), 2.39-2.31 (2H, m), 2.06-1.93 (1H, m), 1.89-1.79 (2H, m), 1.39-1.18 (9H, m).

EXAMPLE 26

N-{2-[4-[N-(4-Piperidyl)glycyl]-piperazin-1-yl]-1,1-dimethyl-2-oxo-ethyl}-2,4-dichloro-3-(2-methyl-8-quinolinoxymethyl)-benzenesulfonamide tris trifluoroacetate HPLC: $t_R$=7.42 min; MS: [M+H]$^+$=691.2. $^1$H NMR (DMSO-d$_6$) δ: 9.16-9.01 (2H, m), 8.76-8.65 (2H, m), 8.43-8.22 (1H, m), 8.07 (1H, d), 7.82 (1H, d), 7.62-7.37 (4H, m), 5.56 (2H, s), 4.25-4.15 (2H, m), 3.01-2.88 (2H, m), 2.62 (3H, s), 2.27-2.18 (2H, m), 1.80-1.64 (2H, m), 1.25 (6H, s).

EXAMPLE 27

N-{2-[4-(4-(2-Aminoethyl)piperazin-1-yl)acetyl)-piperazin-1-yl]-1,1-dimethyl-2-oxo-ethyl}-2,4-dichloro-3-(2-methyl-8-quinolinoxymethyl)-benzenesulfonamide tetra trifluoroacetate HPLC: $t_R$=7.59 min; MS: [M+H]$^+$=720.2; $^1$H NMR (DMSO-d$_6$) δ: 8.74 (1H, s), 8.52-8.32 (1H, brs), 8.08 (1H, d), 7.83 (1H, d), 7.79-7.45 (6H, m), 5.58 (2H, s), 3.69-3.55 (2H, m), 3.54-3.41 (2H, m), 3.00-2.90 (2H, m), 2.68 (3H, s), 2.65-2.54 (2H, m), 1.25 (6H, s).

EXAMPLE 28

N-{2-[4-(3-(R)-Amino-6-guanidino-hexanoyl)-piperazin-1-yl]-1,1-dimethyl-2-oxo-ethyl}-2,4-dichloro-3-(2-methyl-8-quinolinoxymethyl)-benzenesulfonamide tris trifluoroacetate HPLC: $t_R$=7.42 min; MS: [M+H]$^+$=721.1; $^1$H NMR (DMSO-d$_6$) δ: 8.71 (1H, s), 8.35-8.24 (1H, brs), 8.23-8.02 (3H, m), 8.07 (1H, d), 7.82 (1H, d), 7.65-7.37 (5H, m), 5.57 (2H, s), 4.52-4.42 (1H, m), 3.13-3.04 (2H, m), 2.64 (3H, s), 1.76-1.63 (2H, m), 1.56-1.17 (11H, m).

EXAMPLE 29

N-{2-[4-(3-(S)-Amino-6-dimethylamino-hexanoyl)-piperazin-1-yl]-1,1-dimethyl-2-oxo-ethyl}-2,4-dichloro-3-(2-methyl-8-quinolinoxymethyl)-benzenesulfonamide tris trifluoroacetate HPLC: $t_R$=7.64 min; MS: [M+H]$^+$=707.1. $^1$H NMR (DMSO-d$_6$) δ: 9.59-9.44 (1H, brs), 8.70 (1H, s), 8.24 (1H, brd), 8.06 (1H, d), 7.89-7.76 (4H, m), 7.60-7.28 (5H, m), 5.56 (2H, s), 3.09-3.00 (2H, m), 2.88-2.73 (7H, m), 2.66-2.59 (3H, m), 1.78-1.52 (4H, m), 1.30-1.21 (6H, m).

EXAMPLE 30

N-{2-[4-(3-(S)-Amino-7-dimethylamino-heptanoyl)-piperazin-1-yl]-1,1-dimethyl-2-oxo-ethyl}-2,4-dichloro-3-(2-methyl-8-quinolinoxymethyl)-benzenesulfonamide tris trifluoroacetate HPLC: $t_R$=7.59 min; MS: [M+H]$^+$=721.2. $^1$H NMR (DMSO-d$_6$) δ: 9.52-9.40 (1H, brs), 8.70 (1H, s), 8.27 (1H, brd), 8.06 (1H, d), 7.84-7.71 (3H, m), 7.82 (1H, d), 7.61-7.28 (5H, m), 5.57 (2H, s), 3.04-2.96 (2H, m), 2.80-2.75 (6H, m), 2.63 (3H, s), 1.65-1.53 (4H, m), 1.40-1.30 (2H, m), 1.25 (6H, s).

EXAMPLE 31

N-(3-Amino-propyl)-4-{2-[2,4-dichloro-3-(2-methyl-quinolin-8-yloxymethyl)-benzenesulfonylamino]-2-methyl-propionyl}-piperazine-1-carboxamidine tris trifluoroacetate HPLC: $t_R$=8.50 min; MS: [M+H]$^+$=650.2; $^1$H NMR (DMSO-d$_6$) δ: 8.70 (1H, s), 8.36-8.27 (1H, m), 8.06 (1H, d), 7.85-7.71 (7H, m), 7.63-7.39 (4H, m), 5.58 (2H, s), 3.30-3.22 (2H, m), 2.90-2.79 (2H, m), 2.64 (3H, s), 1.85-1.74 (2H, m), 1.24 (6H, s).

EXAMPLE 32

N-[2-[4-(2-(S)-Amino-5-dimethylamino-pentanoyl))-piperazin-1-yl]-1,1-dimethyl-2-oxo-ethyl}-2,4-dichloro-3-(2-methyl-8-quinolinoxymethyl)-benzenesulfonamide tris trifluoroacetate HPLC: $t_R$=7.28 min; MS: [M+H]$^+$=693.1. $^1$H NMR (DMSO-d$_6$) d: 9.68-9.40 (1H, m), 8.76 (1H, s), 8.33-8.16 (4H, m), 8.06 (1H, d), 7.83 (1H, d), 7.62-7.35 (4H, m), 5.56 (2H, s), 4.60-4.45 (1H, m), 3.12-3.01 (2H, m), 2.79-2.73 (6H, m), 2.62 (3H, s), 1.78-1.59 (4H, m), 1.32-1.19 (6H, m).

EXAMPLE 33

(S)—N-{2-[1'-(2-Amino-5-guanidino-pentanoyl)-[4,4']bipiperidinyl-1-yl]-1,1-dimethyl-2-oxo-ethyl}-2,4-dichloro-3-(2-methyl-quinolin-8-yloxymethyl)-benzenesulfonamide HPLC: $t_R$=7.96 min; MS: [M+H]$^+$=789.5; $^1$H NMR (DMSO-d$_6$): 8.57 (s, 1H); 8.22 (d, 1H); 8.06 (bs, 2H); 8.05-8.04 (d, 1H); 7.80 (d, 1H); 7.56-7.36 (5H); 5.55 (s, 2H); 3.92-3.84 (m, 1H); 3.11-3.01 (m, 4H); 2.60 (s, 3H); 1.80-0.99 (22H).

EXAMPLE 34

2,4-Dichloro-N-(2-{4-[2-(3,5-dimethyl-piperazin-1-yl)-ethyl]-3,5-dimethyl-piperazin-1-yl}-1,1-dimethyl-2-oxo-ethyl)-3-(2-methyl-4a,8a-dihydro-quinolin-8-yloxymethyl)-benzenesulfonamide HPLC: $t_R$=5.87 min; MS: [M+H]$^+$=719.2; $^1$H NMR (DMSO-d$_6$): 8.90 (d, 1H); 8.76 (s, 1H); 8.27-8.18 (m, 2H); 8.05 (d, 1H); 7.85 (d, 1H); 7.56-7.36 (3H); 5.57 (s, 2H); 2.62 (s, 3H); 2.00-2.04 (t, 2H); 1.34-1.16 (18H).

EXAMPLE 35

N-(2-{4-[4-(2-(S)Amino-5-guanidino-pentanoyl)-piperazin-1-yl]-piperidin-1-yl}-1,1-dimethyl-2-oxo-ethyl)-2,4-dichloro-3-(2-methyl-quinolin-8-yloxymethyl)-benzenesulfonamide HPLC: $t_R$=6.65 min; MS: [M+H]$^+$=790.4; $^1$H NMR (DMSO-d$_6$): 8.57 (s, 1H); 8.22 (d, 1H); 8.06 (bs, 2H); 8.05 (d, 1H); 7.80 (d, 1H); 7.56-7.36 (5H); 5.60 (s, 2H); 4.53-4.37 (4H); 2.62 (s, 3H); 1.82-1.45 (8H); 1.28-1.12 (9H)

EXAMPLE 36

2,4-Dichloro-3-(2,4-dimethyl-quinolin-8-yloxymethyl)-benzenesulfinic acid [1-(4-piperazin-1-yl-piperidine-1-carbonyl)-cyclopentyl]-amide HPLC: $t_R$=5.70 min; MS: [M+H]$^+$=674.3; $^1$H NMR (DMSO-d$_6$): 8.57 (s, 1H); 8.22 (d, 1H); 8.06 (bs, 2H); 8.04 (d, 1H); 7.80 (d, 1H); 7.56-7.36 (5H); 5.60 (s, 2H); 4.53-4.37 (4H); 2.62 (s, 3H); 1.82-1.45 (8H); 1.28-1.12 (9H)

EXAMPLE 37

2,4-Dichloro-3-(2,4-dimethyl-quinolin-8-yloxymethyl)-benzenesulfinic acid (1-{4-[4-(2-S-amino-6-guanidino-hexanoyl)-piperazin-1-yl]-piperidine-1-carbonyl}-cyclopentyl)-amide HPLC: $t_R$=7.29 min; MS: [M+H]$^+$=844.4; $^1$H NMR (DMSO-d$_6$): 8.57 (s, 1H); 8.3-8.1 (bs, 3H); 8.02 (d, 1H); 7.82 (d, 1H); 5.58 (s, 2H); 4.65-4.48 (m, 4H); 3.08 (m, 1H); 2.69 (s, 3H); 2.61 (m, 3H)

EXAMPLE 38

2,4-Dichloro-3-(2,4-dimethyl-quinolin-8-yloxymethyl)-benzenesulfinic acid (1-{4-[4-(2-S-amino-5-guanidino-pentanoyl)-piperazin-1-yl]-piperidine-1-carbonyl}-cyclopentyl)-amide HPLC: $t_R$=7.26 min; MS: [M+H]$^+$=830.4; $^1$H NMR (DMSO-d$_6$): 8.58 (s, 1H); 8.17 (bs, 3H); 8.02 (d, 1H); 7.82 (d, 1H); 5.58 (s, 2H); 4.65-4.28 (m, 5H); 3.11 (m, 1H); 2.69 (s, 3H); 2.61 (m, 3H)

EXAMPLE 39

2,4-Dichloro-3-(2,4-dimethyl-quinolin-8-yloxymethyl)-benzenesulfinic acid [1-(4-piperidin-4-yl-piperazine-1-carbonyl)-cyclopentyl]-amide HPLC: $t_R$=7.59 min; MS: [M+H]$^+$=674.3; $^1$H NMR (DMSO-d$_6$): 8.8-8.3 (bs, 3H); 8.02 (d, 1H); 7.82 (d, 1H); 7.80-7.25 (5H); 5.57 (s, 2H); 4.52 (bs, 2H); 2.92 (m, 4H); 2.66 (s, 3H); 2.59 (s, 3H); 2.30-1.60 (9H); 1.44 (m, 4H)

EXAMPLE 40

2,4-Dichloro-3-(2-methyl-quinolin-8-yloxymethyl)-benzenesulfinic acid {2-[4-(2-guanidino-ethyl)-piperazin-1-yl]-1,1-dimethyl-2-oxo-ethyl}-amide HPLC: $t_R$=5.68 min; MS: [M+H]$^+$=636.3; $^1$H NMR (DMSO-d$_6$): 8.69 (s, 1H); 8.32 (bs, 1H); 8.06 (d, 1H); 7.82 (d, 1H); 7.6-7.4 (7H); 5.57 (s, 2H); 3.6-3.5 (m, 4H); 2.65 (s, 3H)

EXAMPLE 41

2,4-Dichloro-3-(2-methyl-quinolin-8-yloxymethyl)-benzenesulfinic acid (2-{4-[2-S-amino-5-(N',N''-diethyl-guanidino)-pentanoyl]-piperazin-1-yl}-1,1-dimethyl-2-oxo-ethyl)-amide HPLC: $t_R$=7.31 min; MS: [M+H]$^+$=763.4; $^1$H NMR (DMSO-d$_6$): 8.71 (s, 1H); 8.22 (m, 3H); 8.05 (d, 1H); 7.82 (d, 1H); 7.57 (d, 1H); 7.52-7.34 (5H); 5.55 (s, 2H); 4.50 (s, 1H); 3.19 (m, 4H); 2.62 (s, 3H); 1.69 (m, 2H); 1.54 (m, 2H); 1.25 (s, 3H); 1.23 (s, 3H); 1.10 (t, 6H)

EXAMPLE 42

2,4-Dichloro-3-(2-methyl-quinolin-8-yloxymethyl)-benzenesulfinic acid (2-{4-[2-R-amino-5-(N',N''-diethyl-guanidino)-pentanoyl]-piperazin-1-yl}-1,1-dimethyl-2-oxo-ethyl)-amide HPLC: $t_R$=7.31 min; MS: [M+H]$^+$=763.3; $^1$H NMR (DMSO-d$_6$): 8.71 (s, 1H); 8.22 (m, 3H); 8.05 (d, 1H); 7.82 (d, 1H); 7.57 (d, 1H); 7.52-7.34 (5H); 5.55 (s, 2H); 4.50 (s, 1H); 3.19 (m, 4H); 2.62 (s, 3H); 1.69 (m, 2H); 1.54 (m, 2H); 1.25 (s, 3H); 1.23 (s, 3H); 1.10 (t, 6H)

EXAMPLE 43

(2S)—N-(1-{4-[2-Amino-6-(N',N"-diethyl-guanidino)-hexanoyl]-piperazine-1-carbonyl}-cyclopentyl)-2,4-dichloro-3-(2,4-dimethyl-quinolin-8-yloxymethyl)-benzenesulfonamide HPLC: $t_R$=8.47 min; MS: [M+H]⁺=817.2; ¹H NMR (DMSO-d₆): 8.62 (s, 1H); 8.14 (s, 3H); 8.02 (d, 1H); 7.74-7.22 (6H); 5.57 (s, 2H); 4.47 (m, 1H); 3.18 (m, 4H); 3.12 (m, 3H); 2.65 (s, 3H); 2.58 (s, 3H); 1.97 (m, 2H); 1.79-1.65 (4H); 1.56-1.25 (8H); 1.10 (t, 6H)

EXAMPLE 44

N-(1-{4-[2-(S)Amino-6-(N',N"-diethyl-guanidino)-pentanoyl]-piperazine-1-carbonyl}-cyclopentyl)-2,4-dichloro-3-(2,4-dimethyl-quinolin-8-yloxymethyl)-benzenesulfonamide HPLC: $t_R$=8.97 min; MS: [M+H]+=803.2; ¹H NMR (DMSO-d₆): 8.62 (s, 1H); 8.14 (s, 3H); 8.02 (d, 1H); 7.74-7.22 (6H); 5.57 (s, 2H); 4.47 (m, 1H); 3.18 (m, 4H); 3.12 (m, 3H); 2.65 (s, 3H); 2.58 (s, 3H); 1.97 (m, 2H); 1.79-1.65 (4H); 1.56-1.25 (8H); 1.10 (t, 6H)

EXAMPLE 45

N-[2-[4-(2-(S)-Amino-6-dimethylamino-hexanoyl)-piperazin-1-yl]-1,1-dimethyl-2-oxo-ethyl]-2,4-dichloro-3-(2,4-dimethyl-quinolin-8-yloxymethyl)-benzenesulfonamide ¹H NMR (DMSO-d₆) δ: 9.58-9.44 (1H, brs), 8.73 (1H, s), 8.27-8.11 (3H, m), 8.07 (1H, d), 7.88-7.36 (5H, m), 5.60 (2H, s), 4.56-4.42 (1H, m), 3.07-2.94 (2H, m), 2.81-2.61 (12H, m), 1.79-1.54 (4H, m), 1.46-1.16 (10H, m). HPLC: $t_R$=13.34 min. MS: [M+H]⁺ 721

EXAMPLE 46

N-[2-[4-(3-(S)-Amino-6-dimethylamino-hexanoyl)-piperazin-1-yl]-1,1-dimethyl-2-oxo-ethyl]-2,4-dichloro-3-(2,4-dimethyl-quinolin-8-yloxymethyl)-benzenesulfonamide ¹H NMR (DMSO-d₆) δ: 9.54-9.41 (1H, brs), 8.69 (1H, s), 8.06 (1H, d), 7.88-7.28 (7H, m), 5.57 (2H, s), 3.08-2.99 (2H, m), 2.88-2.73 (7H, m), 2.72-2.57 (6H, m), 1.76-1.53 (4H, m), 1.30-1.20 (7H, m). HPLC: $t_R$=13.56 min.MS: [M+H]⁺ 721

EXAMPLE 47

N-[2-[4-(3-(S)-Amino-6-dimethylamino-heptanoyl)-piperazin-1-yl]-1,1-dimethyl-2-oxo-ethyl]-2,4-dichloro-3-(2,4-dimethyl-quinolin-8-yloxymethyl)-benzenesulfonamide ¹H NMR (DMSO-d₆) δ: 9.51-9.37 (1H, brs), 8.69 (1H, s), 8.06 (1H, d), 7.87-7.29 (7H, m), 5.57 (2H, s), 3.05-2.95 (2H, m), 2.86-2.73 (7H, m), 2.73-2.55 (6H, m), 1.67-1.52 (4H, m), 1.43-1.29 (2H, m), 1.24 (6H, s). HPLC: $t_R$=13.56 min. MS: [M+H]⁺ 735

EXAMPLE 48

N-[2-[4-(2-(S)-Amino-5-guanidino-pentanoyl)-piperazin-1-yl]-1,1-dimethyl-2-oxo-ethyl]-2,4-dichloro-3-(2,4-dimethyl-quinolin-8-yloxymethyl)-benzenesulfonamide ¹H NMR (DMSO-d₆) δ: 8.72 (1H, s), 8.24-8.12 (3H, m), 8.07 (1H, d), 7.86-6.92 (9H, m), 5.60 (2H, s), 4.54-4.44 (1H, m), 3.19-3.07 (2H, m), 2.79-2.61 (6H, m), 1.77-1.46 (4H, m), 1.29-1.20 (6H, m). HPLC: $t_R$=8.32 min. MS: [M+H]⁺ 721

EXAMPLE 49

N-[2-[4-(2-(S)-Amino-6-guanidino-hexanoyl)-piperazin-1-yl]-1,1-dimethyl-2-oxo-ethyl]-2,4-dichloro-3-(2,4-dimethyl-quinolin-8-yloxymethyl)-benzenesulfonamide ¹H NMR (DMSO-d₆) δ: 8.71 (1H, s), 8.24-8.00 (4H, m), 7.88-6.74 (9H, m), 5.59 (2H, s), 4.54-4.40 (1H, m), 3.13-3.03 (2H, m), 2.76-2.59 (6H, m), 1.77-1.62 (2H, m), 1.54-1.43 (2H, m), 1.28-1.22 (6H, m). HPLC: $t_R$=8.38 min. MS: [M+H]⁺ 735

EXAMPLE 50

N-[2-[4-(2-(S)-Amino-5-dimethylamino-pentanoyl))-piperazin-1-yl]-1,1-dimethyl-2-oxo-ethyl]-2,4-dichloro-3-(2,4-dimethyl-quinolin-8-yloxymethyl)-benzenesulfonamide ¹H NMR (DMSO-d₆) d: 9.53-9.40 (1H, brs), 8.72 (1H, s), 8.29-8.13 (3H, m), 8.06 (1H, d), 7.86-7.31 (4H, m), 5.58 (2H, s), 4.57-4.46 (1H, m), 3.12-3.01 (2H, m), 2.80-2.73 (6H, m), 2.73-2.60 (3H, m), 1.80-1.59 (4H, m), 1.33-1.19 (6H, m). HPLC: $t_R$=13.44 min. MS: [M+H]⁺ 707

EXAMPLE 51

N-[2-[4-(2-(R)-Amino-5-guanidino-pentanoyl)-piperazin-1-yl]-1,1-dimethyl-2-oxo-ethyl]-2,4-dichloro-3-(2-methyl-quinolin-8-yloxymethyl)-benzenesulfonamide ¹H NMR (DMSO-d₆) δ: 8.72 (2H, brs), 8.32-8.42 (1H, brs), 8.16-8.22 (3H, brs), 8.17 (1H, d), 7.82 (1H, d), 7.71 (1H, brs), 7.76-6.89 (7H, m), 5.58 (2H, s), 4.49 (1H, brs), 3.13 (1H, brs), 1.63-1.77 (2H, brs), 1.44-1.61 (2H, brs), 1.24 (6H, s). HPLC: $t_R$=7.45 min. MS: [M+H]⁺ 709.

EXAMPLE 52

N-[2-[4-(3-(S)-Amino-6-guanidino-hexanoyl)-piperazin-1-yl]-1,1-dimethyl-2-oxo-ethyl]-2,4-dichloro-3-(2-methyl-quinolin-8-yloxymethyl)-benzenesulfonamide ¹H NMR (DMSO-d₆) δ: 8.94 (2H, s), 8.71(1H, s), 8.31 (1H, s), 8.08 (1H, d), 7.82 (1H, d), 7.75 (3H, brs), 7.63-7.45 (5H, m), 7.44 (1H, d), 7.35-6.60 (4H, m), 5.67 (2H, s), 3.10 (2H, m), 2.82 (2H, m), 2.63 (3H, s), 1.63-1.49 (4H, m), 1.24 (6H, s). HPLC: $t_R$=7.79 min. MS: [M+H]⁺ 721

EXAMPLE 53

N-[2-[4-(3-(S)-Amino-7-guanidino-heptanoyl)-piperazin-1-yl]-1,1-dimethyl-2-oxo-ethyl]-2,4-dichloro-3-(2-methyl-quinolin-8-yloxymethyl)-benzenesulfonamide $^1$H NMR (DMSO-d$_6$) δ: 8.95 (2H, s), 8.59 (1H, s), 8.30 (1H, brs), 8.06 (1H, d), 7.82 (1H, d), 7.75 (3H, brs), 7.65-7.38 (6H, m), 7.37-6.73 (3H, m), 5.68 (2H, s), 3.07 (2H, m), 2.80 (1H, m), 2.67 (1H, m), 2.63 (3H, s), 1.63-1.29 (6H, m), 1.29-1.18 (6H, s). HPLC: $t_R$=7.90 min. MS: [M+H]$^+$ 735

EXAMPLE 54

N-{2-[4-(4-2-(guanidino)ethyl]piperazin-1-ylacetyl)-piperazin-1-yl]-1,1-dimethyl-2-oxo-ethyl]-2,4-dichloro-3-(2-methyl-quinolin-8-yloxymethyl)-benzenesulfonamide $^1$H NMR (DMSO-d$_6$) δ: 8.62 (1H, brs), 8.25 (1H, brs), 8.23 (1H, d), 8.05 (1H, d), 7.76 (1H, d), 7.60-7.33 (5H, m), 7.18-6.99 (5H, brs), 5.68 (2H, s), 4.06 (2H, brs), 3.58 (2H, brs), 3.34 (2H, m), 3.17 (4H, brs), 2.89 (4H, brs), 2.73 (2H, m), 2.67 (3H, s), 1.31 (6H, s). HPLC: $t_R$=7.75 min. MS: [M+H]$^+$ 762

EXAMPLE 55

N-[1-[4-(2-(S)-Amino-5-guanidino-pentanoyl)-piperazine-1-carbonyl]-cyclopentyl]-2,4-dichloro-3-(2-methyl-quinolin-8-yloxymethyl)-benzenesulfonamide tris trifluoroacetate $^1$H NMR (DMSO-d$_6$) d: 8.64 (1H, s), 8.26 (1H, d), 8.15 (2H, brs), 8.05 (1H, d), 7.83 (1H, d), 7.66-7.36 (5H, m), 7.34-6.85 (5H, brs), 5.68 (2H, s), 4.50 (1H, brs), 3.14 (2H, s), 2.63 (3H, s), 2.07-1.38 (12H, m). HPLC: $t_R$=10.63 min. MS: [M+H]$^+$ 733

EXAMPLE 56

N-[1-[4-(2-(S)-Amino-6-guanidino-hexanoyl)-piperazine-1-carbonyl]-cyclopentyl]-2,4-dichloro-3-(2-methyl-quinolin-8-yloxymethyl)-benzenesulfonamide tris trifluoroacetate $^1$H NMR (DMSO-d$_6$) δ: 8.64 (1H, s), 8.28 (1H, brs), 8.14 (2H, brs), 8.03 (1H, d), 7.83 (1H, d), 7.63-7.38 (5H, m), 7.37-6.82 (5H, m), 5.68 (2H, s), 4.47 (1H, brs), 3.07 (2H, m),), 2.62 (3H, s), 2.04-1.90 (2H, brs), 1.84-1.59 (4H, brs), 1.56-1.37 (8H, m). HPLC: $t_R$=10.98 min. MS: [M+H]$^+$ 747

ESEMPIO 57

N-[1-[4-(2-(S)-Amino-6-dimethylamino-hexanoyl)-piperazin-1-yl]-cyclopentyl]-2,4-dichloro-3-(2-methyl-quinolin-8-yloxymethyl)-benzenesulfonamide tris trifluoroacetate $^1$H NMR (DMSO-d$_6$) δ: 9.50 (1H, brs), 8.65 (1H, s), 8.26 (1H, d), 8.22-8.11 (2H, m), 8.03 (1H, d), 7.83 (1H, d), 7.62-7.35 (5H, m), 5.68 (2H, s), 4.56-4.41 (1H, brs), 3.09-2.92 (2H, brs),), 2.77 (6H, s), 2.62 (3H, s), 2.07-1.24 (16H, m). HPLC: $t_R$=8.19 min. MS: [M+H]$^+$ 733

EXAMPLE 58

N-[1-[4-(2-(S)-Amino-6-guanidino-hexanoyl)-piperazine-1-carbonyl]-cyclopentyl]-2,4-dichloro-3-(2,4-dimethyl-quinolin-8-yloxymethyl)-benzenesulfonamide tris trifluoroacetate $^1$H NMR (DMSO-d$_6$) δ: 8.65 (1H, s), 8.14 (3H, brs), 8.04 (1H, d), 7.83 (1H, d), 7.81-7.44 (5H, m), 7.39-6.76 (3H, s), 5.50 (2H, s), 4.46 (1H, brs), 3.07 (2H, m), 2.72 (3H, s), 2.67 (3H, s), 2.03-1.91 (2H, m), 1.80-1.61 (4H, m), 1.53-1.25 (10H, m). HPLC: $t_R$=8.80 min. MS: [M+H]$^+$ 761

EXAMPLE 59

N-[1-[4-(2-(S)-Amino-6-dimethylamino-hexanoyl)-piperazin-1-yl]-cyclopentyl]-2,4-dichloro-3-(2,4-dimethyl-quinolin-8-yloxymethyl)-benzenesulfonamide tris trifluoroacetate $^1$H NMR (DMSO-d$_6$) δ: 9.44 (1H, brs), 8.64 (1H, s), 8.23-8.10 (3H, brs), 8.03 (1H, d), 7.83 (1H, d), 7.75 (1H, brs), 7.69-7.33 (8H, m), 5.59 (2H, s), 4.48 (1H, brs), 3.00 (1H, m), 2.78 (6H, s), 2.74-2.58 (4H, m), 2.60 (6H, s), 2.06-1.23 (14H, m). HPLC: $t_R$=8.96 min. MS: [M+H]$^+$ 747

EXAMPLE 60

(R)—N-[4-(2-(S)-amino-6-guanidino-hexanoyl)-piperazine-1-carbonyl]-1-methyl-propyl]-2,4-dichloro-3-(2,4-dimethyl-quinolin-8-yloxymethyl)-benzenesulfonamide tris trifluoroacetate $^1$H NMR (DMSO-d$_6$) δ: 8.60 (1H, s), 8.13 (3H, brs), 8.06 (1H, d), 7.82 (1H, d), 7.79-6.70 (8H, m), 5.59 (2H, s), 4.46 (1H, brs), 4.33-3.34 (8H, m), 3.07 (2H, m), 2.71 (3H, s), 2.56 (3H, s), 1.86-1.20 (8H, m), 1.09 (3H, s), 0.69 (3H, t).HPLC: $t_R$=8.77 min. MS: [M+H]$^+$ 749

EXAMPLE 61

(R)—N-[1-[4-(2-(S)-Amino-6-dimethylamino-hexanoyl)-piperazine-1-carbonyl]-1-methyl-propyl]-2,4-dichloro-3-(2,4-dimethyl-quinolin-8-yloxymethyl)-benzenesulfonamide tris trifluoroacetate $^1$H NMR (DMSO-d$_6$) δ: 9.43 (1H, s), 8.60 (1H, s), 8.15 (3H, brs), 8.05 (1H, d), 7.82 (1H, d), 7.78-7.31 (4H, m), 5.58 (2H, s), 4.47 (1H, s), 3.74 (8H, m), 3.00 (2H, m), 2.77 (6H, s), 2.68 (3H, s), 2.60 (3H, s), 1.87-1.53 (8H, m), 1.10 (3H, s), 0.71 (3H, t). HPLC: $t_R$=8.53 min. MS: [M+H]$^+$ 735

EXAMPLE 62

N-{2-[4-(4-2(Guanidino)ethyl]piperazin-1-ylacetyl)-piperazin-1-carbonyl]-cyclopentyl]-2,4-dichloro-3-(2,4-dimethyl-quinolin-8-yloxymethyl)-benzenesulfonamide tetra trifluoroacetate $^1$H NMR (DMSO-d$_6$) δ: 8.45 (1H, s), 8.02 (1H, d), 7.77 (1H, d), 7.76-7.33 (4H, m), 7.25-7.12 (4H, brs), 5.68 (2H, s), 4.25-4.10 (2H, brs), 3.75-2.76 (16H, m), 2.75 (3H, s), 2.70 (3H, s), 2.10-0.90-(8H, m). HPLC: $t_R$=8.90 min. MS: [M+H]$^+$ 802

EXAMPLE 63

N-[1-[4-(2-(R)-Amino-6-amino-hexanoyl)-piperazine-1-carbonyl]-cyclopentyl]-2,4-dichloro-3-(2,4-dimethyl-quinolin-8-yloxymethyl)-benzenesulfonamide tris trifluoroacetate $^1$H NMR (DMSO-d$_6$) δ: 8.42 (1H, s), 8.09 (3H, brs), 8.02 (1H, d), 7.78 (1H, d), 7.72 (1H, d), 7.70 (3H, brs), 7.51 (1H, t), 7.39 (1H, d), 7.34 (1H, s), 5.53 (2H, s), 4.41 (1H, brs), 3.84-3.46 (8H, m), 2.80 (2H, brs), 2.68 (3H, s), 2.62 (3H, s), 1.85-1.23 (14H, m). HPLC: t$_R$=8.58 min. MS: [M+H]$^+$ 719

EXAMPLE 64

N-[1-[4-(2-(R)-Amino-6-guanidino-hexanoyl)-piperazine-1-carbonyl]-cyclopentyl]-2,4-dichloro-3-(2,4-dimethyl-quinolin-8-yloxymethyl)-benzenesulfonamide tris trifluoroacetate hu 1H NMR (DMSO-d$_6$) δ: 8.42 (1H, s), 8.08 (3H, brs), 8.02 (1H, d), 7.79 (1H, d), 7.74 (1H, d), 7.50-7.34 (3H, m), 7.07-6.93 (4H, brs), 5.54 (2H, s), 4.42 (1H, brs), 3.73 (8H, m), 3.11 (2H, m), 2.68 (3H, s), 2.63 (3H, s), 2.08-1.22 (14H, m). HPLC: t$_R$=8.74 min. MS: [M+H]$^+$ 761

EXAMPLE 65

N-[2-[4-(3-(S)-Amino-6-guanidino-hexanoyl)-piperazin-1-carbonyl]-cyclopentyl]-2,4-dichloro-3-(2,4-dimethyl-quinolin-8-yloxymethyl)-benzenesulfonamide tris trifluoroacetate $^1$H NMR (DMSO-d$_6$) δ: 8.44 (1H, s), 8.02 (1H, d), 7.79 (1H, d), 7.77-7.67 (3H, m), 7.50 (1H, t), 7.43 (1H, t), 7.37 (1H, d), 7.32 (1H, brs), 7.10-6.90 (4H, brs), 5.61 (2H, s), 3.77-3.41 (9H, m), 3.02 (2H, m), 2.79-2.68 (2H, m), 2.66 (3H, s), 2.59 (3H, s), 2.06-1.37 (12H, m). HPLC: t$_R$=9.02 min. MS: [M+H]$^+$ 761

EXAMPLE 66

N-[2-[4-(3-(S)-Amino-6-dimethylamino-hexanoyl)-piperazin-1-carbonyl]-cyclopentyl]-2,4-dichloro-3-(2,4-dimethyl-quinolin-8-yloxymethyl)-benzenesulfonamide tris trifluoroacetate $^1$H NMR (DMSO-d$_6$) δ: 9.47 (1H, brs), 8.61 (1H, s), 8.03 (1H, d), 7.82 (1H, d), 7.81 (3H, s), 7.68 (1H, d), 7.51 (1H, t), 7.39 (1H, d), 7.32 (1H, brs), 5.55 (2H, s), 3.52 (8H, m), 3.03-2.84 (2H, brs), 2.76 (3H, s), 2.63 (3H, s), 2.56 (3H, s), 2.03-1.34 (10H, m). HPLC: t$_R$=8.85 min. MS: [M+H]$^+$ 747

EXAMPLE 67

N-[1-[4-(6-Guanidino-hexanoyl)-piperazine-1-carbonyl]-cyclopentyl]-2,4-dichloro-3-(2,4-dimethyl-quinolin-8-yloxymethyl)-benzenesulfonamide bis trifluoroacetate $^1$H NMR (DMSO-d$_6$) δ: 8.44 (1H, s), 8.02 (1H, d), 7.79 (1H, d), 7.76-7.32 (5H, m), 7.05-6.84 (4H, brs), 5.55 (2H, s), 3.66-3.47 (8H, m), 3.10 (2H, m), 2.68 (3H, s), 2.52 (3H, s), 2.38-2.32 (2H, m), 2.08-1.23 (14H, m). HPLC: t$_R$=10.17 min. MS: [M+H]$^+$ 746

EXAMPLE 68

N-[2-[4-(2-(S)-Amino-6-amino-hexanoyl)-piperazin-1-yl]-1,1-dimethyl-2-oxo-ethyl]-2,4-dichloro-3-(2-methyl-quinolin-8-yloxymethyl)-benzenesulfonamide tris trifluoroacetate $^1$H NMR (DMSO-d$_6$) δ: 8.72 (1H, m), 8.37-8.28 (1H, d), 8.18-8.11 (3H, d), 8.07 (1H, d), 7.83 (1H, d), 7.76-7.67 (3H, brs), 7.64-7.40 (4H, m), 5.49 (2H, s), 4.45 (1H, s), 3.65-3.43 (8H, m), 2.83-2.72 (2H, m), 2.65 (3H, s), 1.77-1.31 (6H, m), 1.25 (6H, s). HPLC: t$_R$=7.30 min. MS: [M+H]$^+$ 679

EXAMPLE 69

N-[2-[4-(2-(S)-Guanidino-6-guanidino-hexanoyl)-piperazin-1-yl]-1,1-dimethyl-2-oxo-ethyl]-2,4-dichloro-3-(2-methyl-quinolin-8-yloxymethyl)-benzenesulfonamide tris trifluoroacetate $^1$H NMR (DMSO-d$_6$) δ: 8.44 (1H, s), 8.24 (1H, d), 8.06 (1H, d), 7.79 (1H, d), 7.58 (1H, d), 7.61-7.34 (4H, m), 5.65 (2H, s), 4.78 (1H, m), 3.95-3.46 (8H, m), 3.11 (2H, m), 2.65 (3H, s), 1.79-1.31 (6H, m), 1.28 (6H, s). HPLC: t$_R$=8.04 min. MS: [M+H]$^+$ 763

EXAMPLE 70

(R)—N-[4-(3-(S)-Amino-6-guanidino-hexanoyl)-piperazine-1-carbonyl]-1-methyl-propyl]-2,4-dichloro-3-(2,4-dimethyl-quinolin-8-yloxymethyl)-benzenesulfonamide tris trifluoroacetate $^1$H NMR (DMSO-d$_6$) δ: 8.29 (1H, s), 8.64 (1H, d), 7.78 (1H, d), 7.77-7.69 (3H, m), 7.56-7.31 (4H, m), 7.10-6.96 (4H, brs), 5.64 (2H, s), 3.74-3.14 (11H, m), 2.86-2.76 (2H, m), 2.68 (3H, s), 2.62 (3H, s), 1.91-1.53 (6H, m), 1.14 (6H, s). HPLC: t$_R$=9.00 min. MS: [M+H]$^+$ 749

EXAMPLE 71

(R)—N-{2-[4-(4-2(Guanidino)ethyl]piperazin-1-ylacetyl)-piperazin-1-carbonyl]-1-methyl-propyl]-2,4-dichloro-3-(2,4-dimethyl-quinolin-8-yloxymethyl)-benzenesulfonamide tetra trifluoroacetate $^1$H NMR (DMSO-d$_6$) δ: 8.32 (1H, s), 8.05 (1H, d), 7.78 (1H, d), 7.76-7.33 (5H, m), 7.20-7.07 (4H, m), 5.65 (2H, s), 4.24-4.03 (2H, brs), 3.65-3.68 (8H, m), 3.00-2.77 (4H, m), 2.59 (3H, s), 2.54 (3H, s), 1.92-1.77 (1H, m), 1.75-1.63 (1H, m), 1.13 (3H, s), 0.72 (3H, s). HPLC: t$_R$=8.94 min. MS: [M+H]$^+$ 790

EXAMPLE 72

(R)—N-[4-(3-(S)-Amino-6-amino-hexanoyl)-piperazine-1-carbonyl]-1-methyl-propyl]-2,4-dichloro-3-(2,4-dimethyl-quinolin-8-yloxymethyl)-benzenesulfonamide tris trifluoroacetate $^1$H NMR (DMSO-d$_6$) δ: 8.58 (1H, s), 8.06 (1H, d), 7.87-7.47 (12H, m), 5.60 (2H, m), 2.84-2.57 (11H, m), 1.87-1.64 (2H, m), 1.66-1.58 (4H, brs), 1.09 (3H, brs), 0.69 (3H, t). HPLC: t$_R$=8.72 min. MS: [M+H]$^+$ 707

EXAMPLE 73

(R)—N-[4-(3-(S)-Guanidino-6-guanidino-hexanoyl)-piperazine-1-carbonyl]-1-methyl-propyl]-2,4-dichloro-3-(2,4-dimethyl-quinolin-8-yloxymethyl)-benzenesulfonamide tris trifluoroacetate $^1$H NMR (DMSO-d$_6$) δ: 8.30 (1H, s), 8.05 (1H, d), 7.77 (1H, d), 7.72 (1H, d), 7.58-7.31 (5H, m), 7.14-6.88 (8H, brs), 5.64 (2H, s), 3.97-3.86 (1H, brs), 3.79-3.44 (8H, m), 3.17-3.10 (3H, m), 2.67 (3H, s), 2.66 (2H, m), 2.66 (2H, m), 2.61 (3H, s), 1.90-1.58 (2H, m), 1.58-1.46 (4H, brs), 1.13 (3H, s), 0.72 (3H, t). HPLC: t$_R$=9.22 minMS: [M+H]$^{++}$ 396

EXAMPLE 74

(R)—N-[4-(3-(S)-Amino-6-dimethylamino-hexanoyl)-piperazine-1-carbonyl]-1-methyl-propyl]-2,4-dichloro-3-(2,4-dimethyl-quinolin-8-yloxymethyl)-benzenesulfonamide tris trifluoroacetate $^1$H NMR (DMSO-d$_6$) δ: 9.48-9.37 (1H, brs), 8.57 (1H, s), 8.05 (1H, d), 7.82 (1H, d), 7.83-7.26 (7H, m), 5.58 (1H, m), 3.83-3.56 (8H, m), 3.09-2.97 (2H, m), 2.77 (6H, s), 2.67 (6H, s), 1.87-1.48 (6H, m), 1.08 (3H, s), 0.70 (3H, t). HPLC: t$_R$=8.81 min. MS: [M+H]$^+$ 735

EXAMPLE 75

(S)—N-[4-(2-(S)-Amino-6-guanidino-hexanoyl)-piperazine-1-carbonyl]-1-methyl-propyl]-2,4-dichloro-3-(2,4-dimethyl-quinolin-8-yloxymethyl)-benzenesulfonamide tris trifluoroacetate $^1$H NMR (DMSO-d$_6$) δ: 8.32 (1H, s), 8.13-8.06 (3H, brs), 8.04 (1H, d), 7.78 (1H, d), 7.76-7.36 (5H, m), 7.09-6.93 (4H, brs), 5.64 (2H, s), 4.47-4.38 (1H, brs), 3.96-3.75 (8H, m), 3.12 (2H, m), 2.70 (3H, s), 2.64 (3H, s), 1.91-1.32 (8H, m), 1.14 (3H, s), 0.72 (3H, t). HPLC: t$_R$=8.64 min.MS: [M+H]$^+$ 749

EXAMPLE 76

(S)—N-[4-(3-(S)-Amino-6-guanidino-hexanoyl)-piperazine-1-carbonyl]-1-methyl-propyl]-2,4-dichloro-3-(2,4-dimethyl-quinolin-8-yloxymethyl)-benzenesulfonamide tris trifluoroacetate $^1$H NMR (DMSO-d$_6$) δ: 8.32 (1H, s), 8.11-8.03 (3H, brs), 8.04 (1H, d), 7.78 (1H, d), 7.71 (1H, d), 7.50 (1H, t), 7.39 (1H, t), 7.32 (1H, brs), 7.06-6.90 (4H, brs), 5.63 (2H, s), 4.47-4.38 (1H, brs), 3.94-3.48 (8H, m), 3.11 (2H, m), 2.67 (3H, s), 2.59 (3H, s), 1.78-1.32 (6H, m), 1.13 (3H, s), 0.72 (3H, t). HPLC: t$_R$=8,94 min. MS: [M+H]$^+$ 749

EXAMPLE 77

2,4-Dichloro-N-{1-[4-(3-(S),6-diamino-hexanoyl)-piperazine-1-carbonyl]-cyclopentyl}-3-(2,4-dimethyl-quinolin-8-yloxymethyl)-benzenesulfonamide tris trifluoroacetate $^1$H NMR (DMSO-d$_6$) δ: 8.62 (1H, s), 8.04 (1H, d), 7.90-7.32 (12H, m), 5.59 (2H, s), 3.58-3.41 (8H, m), 2.86-2.56 (9H, m), 2.03-1.21 (12H, m). HPLC: t$_R$=8.79 min. MS: [M+H]$^+$ 719

EXAMPLE 78

2,4-Dichloro-N-{1-[4-(3(S),6-diguanidino-hexanoyl)-piperazine-1-carbonyl]-cyclopentyl}-3-(2,4-dimethyl-quinolin-8-yloxymethyl)-benzenesulfonamide tris trifluoroacetate $^1$H NMR (DMSO-d$_6$) δ: 8.60 (1H, s), 8.03 (1H, d), 7.82 (1H, d), 7.78-6.72 (15H, m), 5.57 (2H, s), 3.95-3.83 (1H, brs), 3.15-2.56 (4H, m), 2.68 (6H, s), 2.03-1.91 (2H, m), 1.79-1.67 (2H, m), 1.54-1.36 (8H, m). HPLC: t$_R$=9.28 min. MS: [M+H]$^+$ 803

EXAMPLE 79

(Compound of General Formula (I) with $R_4=R_5=CH_3$, $X=Cl$, $R_1=H$, B=

$R_{13}=$—COY, Y=

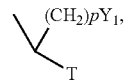

$Y_1=NR_{14}R_{18}R_{19}$, $T=NR_7R_8$, p=4, $R_{14}=R_{18}=R_{19}=CH_3$, $R_7=R_8=H$) N-{1-[4-(2-(S)-Amino-6-trimethylammonium-hexanoyl)-piperazine-1-carbonyl]-cyclopentyl}-2,4-dichloro-3-(2,4-dimethyl-quinolin-8-yloxymethyl)-benzenesulfonamide tris trifluoroacetate $^1$H NMR (DMSO-d$_6$) δ: 8.66 (1H, s), 8.27-8.12 (3H, brs), 8.04 (1H, d), 7.84 (1H, d), 7.81-7.37 (4H, m), 5.60 (2H, s), 4.60-4.42 (1H, brs), 3.70-3.42 (8H, m), 3.24 (2H, m), 3.15 (9H, s), 2.75 (3H, s), 2.67 (3H, s), 2.04-1.93 (2H, m), 1.82-1.22 (14H, m). HPLC: t$_R$=8.61 min. MS: [M]$^+$ 761

EXAMPLE 80

N-(1-{4-[3-(S),6-Bis-(N',N''-dicyclohexyl-guanidino)-hexaoyl]-piperazine-1-carbonyl}-cyclopentyl)-2,4-dichloro-3-(2,4-dimethyl-quinolin-8-yloxymethyl)-benzensulfonamide tris trifluoroacetate $^1$H NMR (DMSO-d$_6$) δ: 8.59 (1H, s), 8.02 (1H, d), 7.82 (1H, d), 7.77-6.88 (10H, m), 5.58 (2H, s), 3.52-3.36 (8H, m), 3.26-3.14 (2H, m), 2.82-2.57 (6H, m), 2.04-1.90 (2H, m), 1.87-1.00 (52H, m). HPLC: t$_R$=16.91 min. MS: [M+H]$^+$ 1131

EXAMPLE 81

N-{1-[4-(2-(S)Amino-3-piperidin-4-yl-propionyl)-piperazine-1-carbonyl]-cyclopentyl}-2,4-dichloro-3-(2,4-dimethyl-quinolin-8-yloxymethyl)-benzene-sulfonamide tris trifluoroacetate $^1$H NMR (DMSO-d$_6$) δ: 8.65-8.45 (1H, brs), 8.40 (1H, s), 8.38-8,20 (3H, m), 8.02 (1H, d), 7.82 (1H, m), 7.78 (3H, m), 7.72 (1H, d), 5.58 (2H, s), 4.40 (1H, m), 3.80-3.52 (8H, m), 3.40-3.25 (2H, m), 2.89 (6H, s), 2.20-1.28 (15H, m). HPLC: t$_R$=8.85 min. MS: [M+H]$^+$ 745

EXAMPLE 82

N-{1-[4-(2-Trimethylammonium-acetyl)-piperazine-1-carbonyl]-cyclopentyl}-2,4-dichloro-3-(2,4-dimethyl-quinolin-8-yloxymethyl)-benzenesulfonamide bis trifluoroacetate $^1$H NMR (DMSO-d$_6$) δ: 8.27 (1H, s), 8.03 (1H, d), 7.77 (1H, d), 7.74-7.37 (4H, m), 5.69 (2H, s), 4.51 (2H, s), 3.75-3.47 (8H, m), 3.29 (9H, s), 2.70 (3H, s), 2.66 (3H, s), 2.11-2.01 (2H, m), 1.84-1.73 (2H, m), 1.53-1.43 (4H, m). HPLC: t$_R$=9.64 min. MS: [M]$^+$ 690

EXAMPLE 83

N-{1-[4-(4-Trimethylammonium-butanoyl)-piperazine-1-carbonyl]-cyclopentyl}-2,4-dichloro-3-(2,4-dimethyl-quinolin-8-yloxymethyl)-benzenesulfonamide bis trifluoroacetate $^1$H NMR (DMSO-d$_6$) δ: 8.25 (1H, s), 8.02 (1H, d), 7.82-7.70 (2H, m), 7.58-7.33 (3H, m), 5.68 (2H, s), 3.64 (4H, brs), 3.55 (4H, brs), 3.37-3.28 (2H, m), 3.10 (9H, s), 2.69 (3H, s), 2.65 (3H, s), 2.50-2.44 (2H, m), 2.11-1.73 (6H, m), 1.55-1.42 (4H, brs). HPLC: t$_R$=9.71 min. MS: [M]$^+$ 718

EXAMPLE 84

N-{1-[4-(3(R)-Hydroxy-4-trimethylammonium-butanoyl)-piperazine-1-carbonyl]-cyclopentyl}-2,4-dichloro-3-(2,4-dimethyl-quinolin-8-yloxymethyl)-benzenesulfonamide bis trifluoroacetate $^1$H NMR (DMSO-d$_6$) δ: 8.27 (1H, s), 8.02 (1H, d), 7.77 (1H, d), 7.76-7.33 (4H, m), 5.68 (2H, s), 4.55-4.47 (1H, m), 3.69-3.49 (8H, m), 3.40 (2H, s), 3.18 (9H, s), 2.58 (3H, s), 2.54 (3H, s), 2.11-2.00 (2H, m), 1.84-1.73 (2H, m), 1.51-1.43 (4H, m). HPLC: t$_R$=9.44 min. MS: [M]$^+$ 734

EXAMPLE 85

N-[1-[4-(2-(S)-Dimethylamino-6-dimethylamino-hexanoyl)-piperazin-1-yl]-cyclopentyl]-2,4-dichloro-3-(2,4-dimethyl-quinolin-8-yloxymethyl)-benzene-sulfonamide tris trifluoroacetate $^1$H NMR (DMSO-d$_6$) δ: 9.40 (1H, brs), 8.32 (1H, s), 8.02 (1H, d), 7.77 (1H, d), 7.76-7.33 (4H, m), 5.68 (2H, s), 4.48 (1H, brs), 3.89-3.45 (8H, m), 3.18-3.04 (2H, m), 2.81 (3H, s), 2.79 (3H, s), 2.68 (3H, s), 2.64 (3H, s), 2.09-1.28 (10H, m). HPLC: t$_R$=8.65 min. MS: [M+H]$^+$ 775

EXAMPLE 86

{5-[(1-{1-[2,4-Dichloro-3-(2,4-dimethyl-quinolin-8-yloxymethyl)-benzensulfonylamino]-cyclopentan-ecarbonyl}-piperidin-4-ylmethyl)-dimethyl-ammonium]-pentyl}-trimethyl-ammonium tris trifluoroacetate HPLC: t$_R$=7.60 min. MS: [M+H]$^+$ 775.9

EXAMPLE 87

{5-[(1-{1-[2,4-Dichloro-3-(2,4-dimethyl-quinolin-8-yloxymethyl)-benzensulfonylamino]-cyclopentan-ecarbonyl}-piperidine-4-carbonyl)-amino]-pentyl}-trimethyl-ammonium bis trifluoroacetate salt HPLC: t$_R$=8.20 min. MS: [M+H]$^+$ 761.8

EXAMPLE 88

N-[1-[4-(2-(S)-Trimethylammonium-6-trimethylammonium-hexanoyl)-piperazin-1-yl]-cyclopentyl]-2,4-dichloro-3-(2,4-dimethyl-quinolin-8-yloxymethyl)-benzenesulfonamide tris trifluoroacetate $^1$H NMR (DMSO-d$_6$) δ: 8.32 (1H, s), 8.02 (1H, d), 7.78 (1H, d), 7.73 (1H, d), 7.59-7.31 (3H, m), 5.68 (2H, s), 4.68-4.60 (1H, m), 4.01-3.56 (8H, m), 3.36-3.28 (2H, m), 3.22 (9H, s), 3.08 (9H, s), 2.68 (3H, s), 2.63 (3H, s), 2.13-1.43 (14H, m). HPLC: t$_R$=8.80 min. MS: [M]$^{++}$ 402

EXAMPLE 89

N-[1-[4-(2-(R)-Trimethylammonium-6-trimethylammonium-hexanoyl)-piperazin-1-yl]-cyclopentyl]-2,4-dichloro-3-(2,4-dimethyl-quinolin-8-yloxymethyl)-benzenesulfonamide tris trifluoroacetate $^1$H NMR (DMSO-d$_6$) δ: 8.30 (1H, s), 8.02 (1H, d), 7.81-7.69 (2H, m), 7.52 (1H, t), 7.43-7.34 (2H, m), 5.67 (2H, s), 4.64 (1H, dd), 3.35-3.28 (1H, m), 3.22 (9H, s), 3.07 (9H, s), 2.68 (3H, s), 2.64 (3H, s), 2.12-1.97 (3H, m), 1.84-1.72 (3H, m), 1.54-1.43 (4H, m), 1.41-1.27 (1H, m), 1.27-1.13 (1H, m). HPLC: t$_R$=7.26 min. MS: [M]$^{++}$ 402

EXAMPLE 90

N-[1-[4-(2-(S)-Trimethylammonium-6-amino-hexanoyl)-piperazin-1-yl]-cyclopentyl]-2,4-dichloro-3-(2,4-dimethyl-quinolin-8-yloxymethyl)-benzene-sulfonamide tris trifluoroacetate $^1$H NMR (DMSO-d$_6$) δ: 8.35 (1H, s), 8.07 (1H, d), 8.01-7.94 (1H, m), 7.87 (2H, s), 7.80 (1H, d), 7.77-7.59 (3H, brs), 5.74 (2H, s), 4.65-4.58 (1H, m), 3.98-3.51 (8H, m), 3.22 (9H, s), 2.91 (6H, s), 2.82-2.80 (2H, m), 2.13-1.41 (14H, m). HPLC: t$_R$=8.64 min. MS: [M]$^+$ 761

EXAMPLE 91

N-{1-[4-(6-Trimethylammonium-hexanoyl)-piperazine-1-carbonyl]-cyclopentyl}-2,4-dichlor-3-(2,4-dimethyl-quinolin-8-yloxymethyl)-benzenesulfonamide bis trifluoroacetate $^1$H NMR (DMSO-d$_6$) δ: 8.30 (1H, s), 8.07 (1H, d), 8.02-7.94 (1H, m), 7.91-7.76 (4H, m), 5.74 (2H, s), 3.67-3.50 (8H, m), 3.34-3.26 (2H, m), 3.07 (9H, s), 2.92 (3H, s), 2.68 (3H, s), 2.91 (3H, s), 2.43-2.36 (2H, m), 2.12-1.33 (14H, m). HPLC: t$_R$=9.99 min. MS: [M]$^+$ 746

EXAMPLE 92

N-(6-Amino-hexyl)-4-{2-[2,4-dichloro-3-(2-methyl-quinolin-8-yloxymethyl)-benzenesulfonylamino]-2-methyl-propionyl}-piperazine-1-carboxamidine $^1$H NMR (DMSO-d$_6$) δ: 8.71 (1H, s), 8.37-8.29 (1H, m), 8.07 (1H, d), 7.82 (1H, d), 7.79-7.64 (5H, m), 7.64-7.41 (3H, m), 5.58 (2H, s), 3.22-3.14 (2H, m), 2.84-2.72 (2H, m), 2.65 (3H, s), 1.59-1.46 (4H, m), 1.35-1.27 (4H, m), 1.24 (6H, s). MS: [M+H]$^+$ 692; HPLC: t$_R$=9.16 min

EXAMPLE 93

N-[2-(3-Amino-propylamino)-ethyl]-4-{2-[2,4-dichloro-3-(2-methyl-quinolin-8-yloxymethyl)-benzenesulfonylamino]-2-methyl-propionyl}-piperazine-1-carboxamidine $^1$H NMR (DMSO-d$_6$) δ: 8.92-8.82 (2H, m), 8.73 (1H, s), 8.39-8.29 (1H, brd), 8.07 (1H, d), 7.98-7.85 (6H, m), 7.82 (1H, d), 7.64-7.41 (4H, m), 5.58 (2H, s), 3.18-3.10 (2H, m), 3.10-3.00 (2H, m), 2.94-2.83 (2H, m), 2.65 (3H, s), 1.96-1.85 (2H, m), 1.25 (6H, s). HPLC: t$_R$=8.20 min.; MS: [M+H]$^+$ 693

EXAMPLE 94

N-(3-Amino-propyl)-4-{2-[2,4-dichloro-3-(2,4-dimethyl-quinolin-8-yloxymethyl)-benzenesulfonylamino]-2-methyl-propionyl}-piperazine-1-carboxamidine bis trifluoroacetate $^1$H NMR (DMSO-d$_6$) δ: 8.57 (1H, s), 8.06 (1H, d), 7.89-7.68 (8H, m), 7.62-7.38 (3H, m), 5.62 (2H, s), 3.32-3.23 (2H, m), 2.92-2.81 (2H, m), 2.69 (3H, s), 2.64 (3H, s), 1.87-1.75 (2H, m), 1.25 (6H, s). HPLC: t$_R$=9.36 min.; MS: [M+H]$^+$ 664

EXAMPLE 95

N-(6-Amino-hexyl)-4-{1-[2,4-dichloro-3-(2,4-dimethyl-quinolin-8-yloxymethyl)-benzenesulfonylamino]-cyclopentanecarbonyl}-piperazine-1-carboxamidine bis trifluoroacetate $^1$H NMR (DMSO-d$_6$) δ: 8.41 (1H, s), 8.02 (1H, d), 7.78 (1H, d), 7.76-7.59 (7H, m), 7.54 (1H, t), 7.43 (1H, d), 7.38 (1H, s), 5.64 (2H, s), 3.76-3.65 (4H, m), 3.55-3.47 (4H, m), 3.24-3.15 (2H, m), 2.85-2.75 (2H, m), 2.69 (3H, s), 2.63 (3H, s), 2.08-1.98 (2H, m), 1.82-1.72 (2H, m), 1.60-1.51 (3H, m), 1.49-1.42 (3H, m), 1.40-1.24 (4H, m). HPLC: t$_R$=10.54 min.; MS: [M+H]$^+$ 732

EXAMPLE 96

N-[2-(3-Amino-propylamino)-ethyl]-4-{1-[2,4-dichloro-3-(2,4-dimethyl-quinolin-8-yloxymethyl)-benzenesulfonylamino]-cyclopentanecarbonyl}-piperazine-1-carboxamidine bis trifluoroacetate $^1$H NMR (DMSO-d$_6$) δ: 8.97-8.69 (1H, brs), 8.42 (1H, s), 8.02 (1H, d), 7.96-7.74 (5H, m), 7.78 (1H, d), 7.72 (1H, d), 7.51 (1H, t), 7.39 (1H, d), 7.34 (1H, s), 5.64 (2H, s), 3.83-3.68 (4H, m), 3.61-3.51 (4H, m), 3.11-3.02 (2H, m), 2.97-2.88 (2H, m), 2.67 (3H, s), 2.61 (3H, s), 2.07-1.89 (4H, m), 1.81-1.71 (2H, m), 1.52-1.42 (4H, m). HPLC: t$_R$=9.34 min.; MS: [M+H]$^+$ 733

EXAMPLE 97

N-[2-(4-{1-[2,4-Dichloro-3-(2,4-dimethyl-quinolin-8-yloxymethyl)-benzenesulfonylamino]-cyclopentanecarbonyl}-piperazin-1-yl)-ethyl]-4-methyl-piperazine-1-carboxamidine bis trifluoroacetate $^1$H NMR (DMSO-d$_6$) δ: 8.64 (1H, s), 8.27-8.07 (2H, m), 8.03 (1H, d), 7.82 (1H, d), 7.79-7.72 (1H, m), 7.70-7.40 (2H, m), 5.60 (2H, s), 2.84 (3H, s), 2.76-2.60 (5H, m), 2.03-1.92 (2H, m), 1.79-1.68 (2H, m), 1.48-1.39 (4, m). HPLC: t$_R$=7.04 min; MS: [M+H]$^+$ 759

EXAMPLE 98

2,4-Dichloro-N-{1-[4-(2(R),6-diamino-hexyl)-piperazine-1-carbonyl]-cyclopentyl}-3-(2,4-dimethyl-quinolin-8-yloxymethyl)-benzenesulfonamide tetra trifluoroacetate $^1$H NMR (DMSO-d$_6$) δ: 8.53 (1H, s), 8.03 (1H, d), 7.87-7.40 (8H, m), 7.83 (1H, d), 5.60 (2H, s), 2.83-2.56 (8H, m), 2.01-1.92 (2H, m), 1.78-1.64 (2H, m), 1.60-1.32 (10H, m). HPLC: t$_R$=7.00 min; MS: [M+H]$^+$ 705

EXAMPLE 99

2,4-Dichloro-N-{1-[4-(2(R),6-diguanidino-hexyl)-piperazine-1-carbonyl]-cyclopentyl}-3-(2,4-dimethyl-quinolin-8-yloxymethyl)-benzenesulfonamide tetrahydrochloride $^1$H NMR (DMSO-d$_6$) δ: 8.81-8.65 (2H, brs), 8.30 (1H, s), 8.03 (1H, d), 7.88-7.63 (3H, m), 7.58-6.91 (13H, m), 5.66 (2H, s), 2.75-2.58 (7H, m), 2.14-1.94 (2H, m), 1.84-1.08 (15H, m). HPLC: t$_R$=7.30 min; MS: [M+H]$^+$ 789

EXAMPLE 100

2,4-Dichloro-3-(2,4-dimethyl-quinolin-8-yloxymethyl)-N-{1-[4-(2-piperazin-1-yl-ethyl)-piperazine-1-carbonyl]-cyclopentyl}-benzenesulfonamide tetra trifluoroacetate $^1$H NMR (DMSO-d$_6$) δ: 8.75-8.62 (3H, m), 8.04 (1H, d), 7.93-7.56 (4H, m), 5.63 (2H, s), 3.39-3.27 (4H, m), 3.19-3.09 (3H, m), 3.04-2.97 (1H, m), 2.87-2.62 (11H, m), 2.04-1.92 (2H, m), 1.77-1.52 (3H, m), 1.49-1.36 (4H, m). HPLC: t$_R$=7.30 min; MS: [M+H]$^+$ 703

EXAMPLE 101

2,4-Dichloro-3-(2,4-dimethyl-quinolin-8-yloxymethyl)-N-{1-[4-(2-piperidin-4-yl-ethyl)-piperazine-1-carbonyl]-cyclopentyl}-benzenesulfonamide $^1$H NMR (DMSO-d$_6$) δ: 8.68 (1H, s), 8.61-8.47 (1H, m), 8.34-8.16 (1H, m), 8.03 (1H, d), 7.93-7.40 (3H, m), 7.84 (1H, d), 7.34-7.17 (2H, m), 5.61 (2H, s), 4.58-4.40 (2H, m), 3.35-3.23 (2H, m), 3.22-3.09 (2H, m), 3.06-2.60 (9H, m), 2.08-1.94 (2H, m), 1.88-1.50 (9H, m), 1.50-1.37 (4H, m), 1.37-1.18 (3H, m). HPLC: t$_R$=7.50 min; MS: [M+H]$^+$ 702

EXAMPLE 102

{3-[(4-{1-[2,4-Dichloro-3-(2,4-dimethyl-quinolin-8-yloxymethyl)-benzenesulfonylamino]-cyclopentanecarbonyl}-piperazine-1-carboximidoyl)-amino]-propyl}-trimethyl-ammonium tris trifluoroacetate $^1$H NMR (DMSO-d$_6$) δ: 8.37-8.26 (1H, m), 8.07-7.98 (1H, m), 7.83-7.66 (4H, m), 7.56-7.46 (1H, m), 7.44-7.31 (2H, m), 5.73-5.64 (2H, m), 3.82-3.71 (4H, m), 3.62-3.52 (5H, m), 3.41-3.26 (4H, m), 3.18-3.06 (9H, m), 2.74-2.60 (6H, m), 2.14-1.96 (5H, m), 1.85-1.73 (2H, m), 1.56-1.43 (4H, m). HPLC: t$_R$=9.90 min; MS: [M]$^+$ 732

EXAMPLE 103

4-{1-[2,4-Dichloro-3-(2,4-dimethyl-quinolin-8-yloxymethyl)-benzenesulfonylamino]-cyclopentanecarbonyl}-N-(3-dimethylamino-propyl)-piperazine-1-carboxamidine tris trifluoroacetate $^1$H NMR (DMSO-d$_6$) δ: 9.78-9.40 (1H, brs), 8.35-8.22 (1H, m), 8.06-7.94 (1H, m), 7.82-7.57 (5H, m), 7.57-7.46 (1H, m), 7.46-7.32 (2H, m), 5.71-5.63 (2H, m), 3.80-3.66 (4H, m), 3.59-3.48 (4H, m), 3.36-3.26 (2H, m), 3.15-3.06 (2H, m), 2.86-2.78 (6H, m), 2.73-2.58 (6H, m), 2.12-1.98 (2H, m), 1.98-1.87 (2H, m), 1.83-1.72 (2H, m), 1.54-1.41 (4H, m). HPLC: t$_R$=10.14 min; MS: [M+H]$^+$ 718

EXAMPLE 104

N-(1-{4-[(5-Amino-pentylamino)-methyl]-piperidine-1-carbonyl}-cyclopentyl)-2,4-dichloro-3-(2,4-dimethyl-quinolin-8-yloxymethyl)-benzenesulfonamide tris trifluoroacetate $^1$H NMR (DMSO-d$_6$) δ: 8.52 (1H, s), 8.47-8.32 (2H, m), 8.03 (1H, d), 7.81 (1H, d), 7.78-7.29 (7H, m), 5.58 (2H, s), 4.44-4.34 (2H, m), 3.06-2.55 (12H, m), 2.02-1.84 (3H, m), 1.82-1.69 (2H, m), 1.68-1.48 (4H, m), 1.48-1.30 (5H, m). HPLC: t$_R$=7.39 min; MS: [M+H]$^+$ 704

EXAMPLE 105

N-{1-[4-(4-Amino-piperidin-1-ylmethyl)-piperidine-1-carbonyl]-cyclopentyl}-2,4-dichloro-3-(2,4-dimethyl-quinolin-8-yloxymethyl)-benzenesulfonamide tris trifluoroacetate $^1$H NMR (DMSO-d$_6$) δ: 9.62-9.24 (1H, m), 8.53 (1H, s), 8.20-7.99 (2H, m), 8.03 (1H, d), 7.86-7.26 (3H, m), 7.82 (1H, d), 5.59 (2H, s), 4.47-4.31 (2H, m), 3.11-2.92 (4H, m), 2.84-2.57 (6H, m), 2.15-1.88 (5H, m), 1.88-1.51 (5H, m), 1.51-1.32 (4H, m). HPLC: t$_R$=7.22 min; MS: [M+H]$^+$ 702

EXAMPLE 106

2,4-Dichloro-3-(2,4-dimethyl-quinolin-8-yloxymethyl)-N-(1-{4-[(5-methylamino-pentylamino)-methyl]-piperidine-1-carbonyl}-cyclopentyl)-benzenesulfonamide tris trifluoroacetate $^1$H NMR (DMSO-d$_6$) δ: 8.32 (2H, brs), 8.17 (1H, s), 8.01 (1H, d), 7.79-7.70 (2H, m), 7.50 (1H, t), 7.37 (1H, d), 7.33 (1H, s), 5.66 (2H, s), 4.42-4.33 (2H, m), 2.98-2.74 (8H, m), 2.67 (3H, s), 2.65-2.57 (5H, m), 2.10-1.88 (3H, m), 1.85-1.74 (4H, m), 1.71-1.57 (4H, m), 1.53-1.14 (8H, m). HPLC: t$_R$=7.56 min; MS: [M+H]$^+$ 718

EXAMPLE 107

[4-(S)-Amino-6-(4-{1-[2,4-dichloro-3-(2,4-dimethyl-quinolin-8-yloxymethyl)-benzenesulfonylamino]-cyclopentanecarbonyl}-piperazin-1-yl)-6-oxohexyl]-trimethylammonium bis trifluoroacetate $^1$H NMR (DMSO-d$_6$) δ: 8.27 (1H, s), 8.08-7.99 (1H, m), 7.95-7.72 (4H, m), 7.59-7.51 (1H, m), 7.47-7.37 (2H, m), 5.68 (2H, m), 3.76-3.48 (8H, m), 3.37-3.24 (2H, m), 3.13-3.06 (9H, m), 2.92-2.79 (1H, m), 2.76-2.63 (7H, m), 2.13-1.99 (2H, m), 1.93-1.74 (3H, m), 1.73-1.60 (2H, m), 1.56-1.42 (4H, m). HPLC: t$_R$=10.26 min. MS: [M+H]$^+$ 761

Biological Activity

The evaluation of the B2 receptor affinity of the compounds of the present invention was carried out with studies of binding to the human B2 receptor expressed in human fibroblasts W138, following the procedure described by Phagoo et al., Br. J. Pharmacol. (1996) 119: 863-868. In the following the binding values are reported expressed as pKi.

The in vivo activity of the compounds of the present invention was evaluated as effectiveness in inhibiting BK-induced bronchospasm in the guinea pig, following the procedure described by Tramontana et al., J. Pharmacol. Exp. Therap., 296:1051-1057, 2001. The compounds of the present invention show higher potency and longer-lasting action than those of molecules of a similar class which however do not contain alpha,alpha dialkyl amino acids.

| Compound (Example N) | pKi | Compound (Example N) | pKi |
|---|---|---|---|
| 25 | 9.27 | 26 | 9.3 |
| 31 | 9.4 | 29 | 9.2 |
| 30 | 9.1 | 20 | 9.2 |
| 45 | 9.2 | 46 | 9.3 |
| 48 | 9.2 | 51 | 9.4 |
| 57 | 9.0 | 59 | 9.0 |
| 93 | 9.0 | 61 | 9.3 |
| 94 | 9.0 | 62 | 9.0 |
| 64 | 9.2 | 65 | 9.1 |
| 66 | 9.1 | 67 | 9.1 |
| 95 | 9.3 | 96 | 9.1 |
| 68 | 9.0 | 70 | 9.2 |
| 71 | 9.4 | 72 | 9.4 |
| 73 | 9.2 | 74 | 9.1 |
| 98 | 9.2 | 80 | 9.2 |
| 81 | 9.2 | 38 | 9.3 |
| 39 | 9.0 | 100 | 9.4 |
| 105 | 9.0 | 82 | 9.2 |
| 83 | 9.4 | 84 | 9.2 |
| 85 | 9.3 | 106 | 9.4 |
| 86 | 9.4 | 107 | 9.7 |
| 88 | 9.7 | 90 | 9.9 |
| 91 | 9.3 | 40 | 9.7 |

-continued

| Compound (Example N) | pKi | Compound (Example N) | pKi |
|---|---|---|---|
| 41 | 9.3 | 42 | 9.4 |
| 43 | 9.4 | 44 | 10.1 |
| 79 | 9.2 | | |

The invention claimed is:

1. A compound of general formula (I):

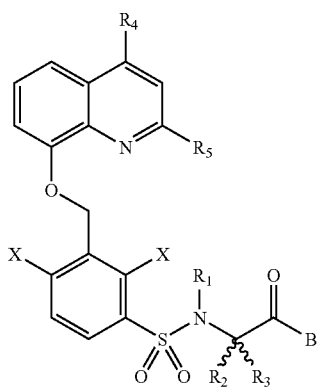

wherein $R_1$ is a hydrogen atom or a $C_1$-$C_4$ alkyl group;

$R_2$ and $R_3$, which can be the same or different, are a $C_1$-$C_4$ alkyl group, or $R_2$ and $R_3$, together with the carbon atom which they are linked to, form a cyclic aliphatic group having 3 to 7 carbon atoms or a heterocyclic aliphatic group having 3 to 7 atoms, one or two of which are selected from the group N, O, S and the others being C atoms;

$R_4$ and $R_5$, which can be the same or different, are a hydrogen atom or a $C_1$-$C_4$ alkyl group;

X is selected from the group consisting of halogen, $OR_1$, $SR_1$, CN, and a $C_1$-$C_4$ alkyl group;

B has at least one amino group with basic characteristics or a tetraalkylammonium group and is selected from the group consisting of:

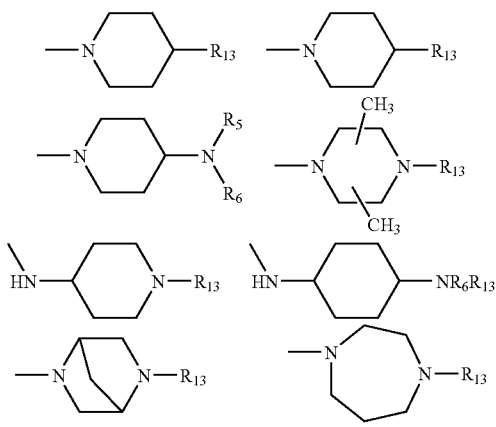

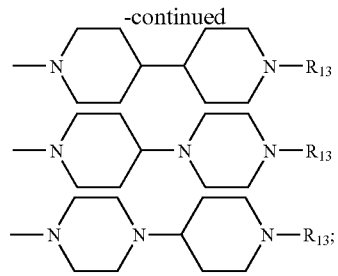

$R_6$ is a hydrogen atom or a $C_1$-$C_6$ alkyl group;

Y is selected from the group consisting of hydrogen, $(CH_2)_p Y_1$, $(CH_2)_p NR_6 Y_1$, $(CH_2)_p N(Y_1)_2$, $NR_5 R_6$, —$NR_6(CH_2)_p Y_1$, and a residue selected from the group consisting of:

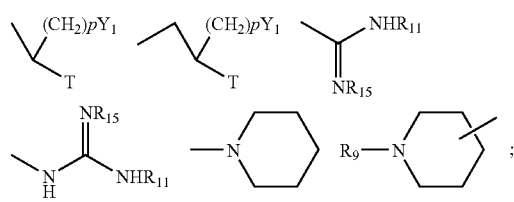

T is selected from the group consisting of —$NR_7 R_8$, —$NR_{14} R_{18} R_{19}$, and —$OR_6$;

$R_7$ and $R_8$, which can be the same or different, are a hydrogen atom, a $C_1$-$C_4$ alkyl group, or $NR_7 R_8$ is a group selected from: i) guanidine optionally substituted with 1 or 2 $C_1$-$C_4$ alkyl groups, cyclohexyl, ii) a 5-7 membered nitrogen heterocycle optionally containing another heteroatom selected from O, N, S;

$Y_1$ is selected from the group consisting of $NR_7 R_8$, $NR_{14} R_{18} R_{19}$, and a residue selected from the group consisting of:

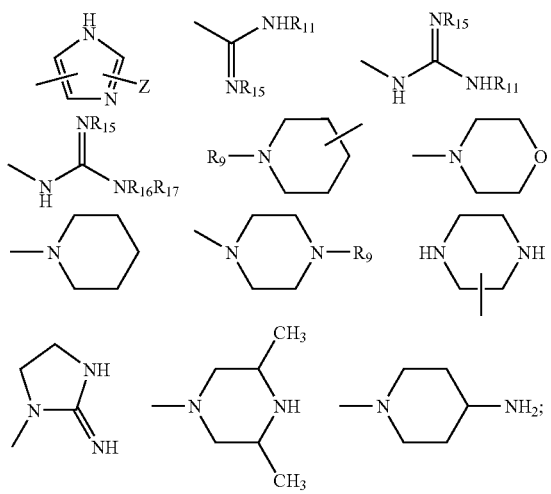

Z is selected from the group consisting of H, $C_1$-$C_6$ alkyl, $OR_6$, $SR_6$, $CF_3$, $OCOR_6$, $COR_{10}$, $NHCOR_6$, $SO_2 R_6$, $SOR_6$, $CO_2 R_6$, $N(R_6)_2$, $C_1$, Br, $NO_2$, $NH_2$, CN, F, imidazole, phenyl, amidine, guanidine, and guanidyl-methyl;

$R_9$ is hydrogen or —$(CH_2)_q$-L, wherein L is selected from the group consisting of —OH, —$NR_5R_6$, —$NR_{14}R_{18}R_{19}$, amidine optionally substituted with 1 or 2 $C_1$-$C_4$ alkyl groups, and guanidine optionally substituted with 1 or 2 $C_1$-$C_4$ alkyl groups;

$R_{10}$ is $OR_6$ or $NR_6R_{12}$;

$R_{11}$ is selected from the group consisting of hydrogen, —$(CH_2)_q$-L, and —$(CH_2)_p$—$NR_4$—$(CH_2)_q$-L;

$R_{12}$ is selected from the group consisting of a hydrogen atom, a $C_1$-$C_6$ alkyl group, and $COR_6$;

$R_{13}$ is selected from the group consisting of H, a —$C_1$-$C_6$ alkyl group, —$(CH_2)_p W(CH_2)_q Y_1$, —Y, —COY, and —$CH_2$—Y;

$R_{14}$ is a straight or branched $C_1$-$C_4$ alkyl group;

$R_{15}$ is selected from the group consisting of hydrogen and straight or branched $C_1$-$C_4$ alkyl groups;

the —$NR_{16}R_{17}$ group is a 5-7 membered nitrogen aliphatic heterocycle optionally containing another heteroatom selected from the group consisting of O, S, and N;

the —$NR_{14}R_{18}R_{19}$ group is a quaternary ammonium group in which: $R_{14}$ is selected from the group consisting of straight or branched $C_1$-$C_4$ alkyl groups, $R_{18}$ and $R_{19}$, which can be the same or different, are a straight or branched $C_1$-$C_4$ alkyl group, or —$NR_{18}R_{19}$ is a 5-7 membered nitrogen heterocycle optionally containing another heteroatom selected from the group consisting of O, N, and S;

W is selected from the group consisting of $CH_2$, O, S, $NR_4$, and $N(R_4)_2$;

p=1-6, q=1-6.

2. The compound according to claim 1, wherein,

B is a residue selected from the group consisting of:

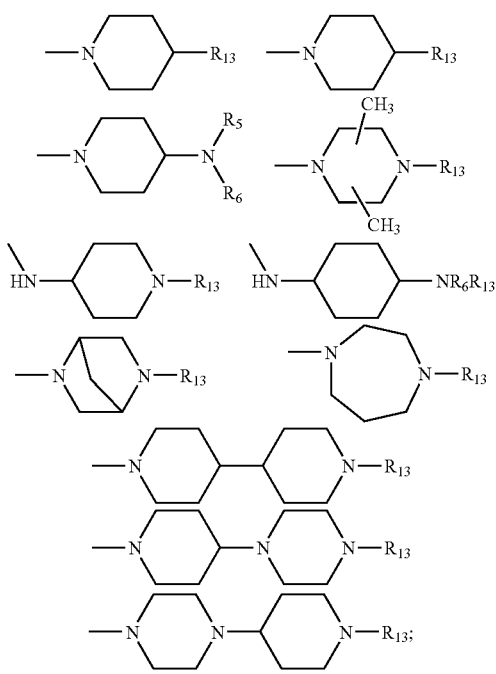

Y is selected from the group consisting of $(CH_2)_p Y_1$, $(CH_2)_p NR_6 Y_1$, $(CH_2)_p N(Y_1)_2$, $NR_5R_6$, and a residue selected from the group consisting of:

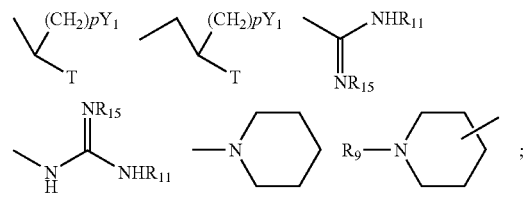

and

T is —$NR_7R_8$, or $OR_6$.

3. The compound according to claim 2, wherein, $R_1$ is a hydrogen atom or methyl;

$R_2$ and $R_3$, which can be the same or different, are methyl or ethyl, or $R_2$ and $R_3$, together with the carbon atom which they are linked to, form a cyclic aliphatic group having 3 to 7 carbon atoms;

$R_4$ and $R_5$, which can be the same or different, are a hydrogen or a methyl;

X is a chlorine atom;

B is a group selected from the group consisting of:

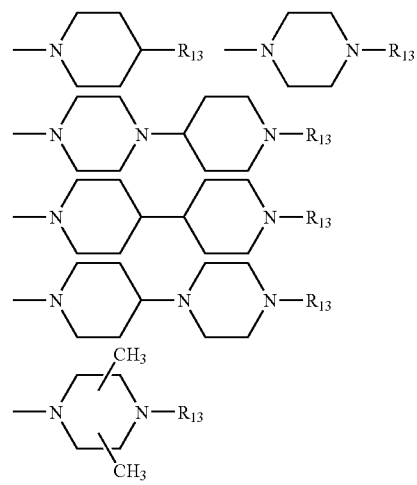

in which $R_{13}$ is H or a Y=$Y_1$ group in which $Y_1$ is

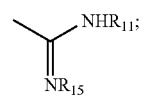

and $R_{11}$ is selected from the group consisting of hydrogen, —$(CH_2)_q$-L, and —$(CH_2)_p$—$NR_4$—$(CH_2)_q$-L, wherein L is selected from the group consisting of —OH, —$NR_5R_6$, amidine optionally substituted with 1 or 2 $C_1$-$C_4$ alkyl groups, and guanidine optionally substituted with 1 or 2 $C_1$-$C_4$ alkyl groups.

4. The compound according to claim 2, wherein, $R_2$ and $R_3$, which can be the same or different, are methyl or ethyl, or $R_2$ and $R_3$, together with the carbon atom which they are linked to, form a cyclic aliphatic group having 3 to 7 carbon atoms;

$R_4$ and $R_5$, which can be the same or different, are a hydrogen or a methyl, X is a chlorine atom;

B contains at least two amino groups with basic characteristics, in free or salified form, and is selected from the group of:

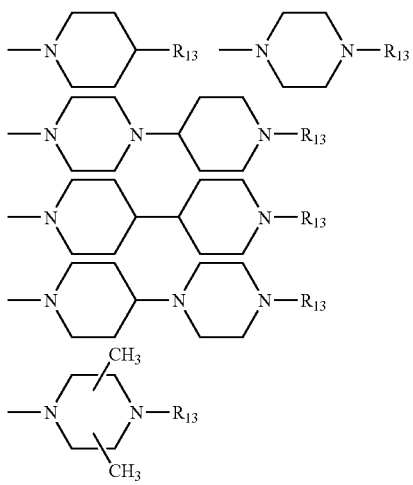

in which $R_{13}$ is COY, $CH_2Y$, $—(CH_2)_pW(CH_2)_qY_1$,
Y is a group $(CH_2)pY_1$, or is selected from:

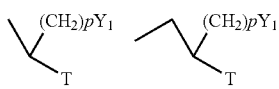

wherein T is $—NR_7R_8$ or $—OR_6$;

$R_7$ and $R_8$, which can be can be the same or different, are selected from the group consisting of a hydrogen atom and a $C_1$-$C_4$ alkyl group, or $NR_7R_8$ is one of i) guanidine optionally substituted with 1 or 2 $C_1$-$C_4$ alkyl groups, cyclohexyl and ii) a 5-7 membered nitrogen heterocycle optionally containing another heteroatom selected from the group consisting of O, N, and S;

$Y_1$ is selected from the group consisting of $—NR_7R_8$ and a residue selected from the group consisting of

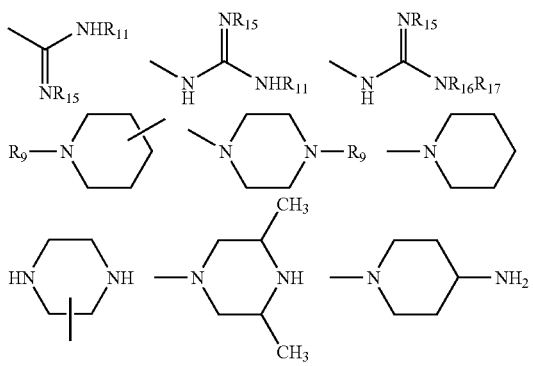

$R_9$ is hydrogen or $—(CH_2)_q$-L, wherein L is selected from the group consisting of $—NR_5R_6$, amidine optionally substituted with 1 or 2 $C_1$-$C_4$ alkyl groups, and guanidine optionally substituted with 1 or 2 $C_1$-$C_4$ alkyl groups.

5. The compound according to claim 1, containing at least one tetralkyl ammonium, wherein $R_1$ is a hydrogen atom or methyl;

$R_2$ and $R_3$, which can be the same or different, are selected from methyl or ethyl, or $R_2$ and $R_3$, together with the carbon atom which they are linked to, form a cyclic aliphatic group having 3 to 7 carbon atoms;

$R_4$ and $R_5$, which can be the same or different, are a hydrogen or a methyl;

X is a chlorine atom;

B is selected from the group consisting of $NR_6Y$ and from the residues:

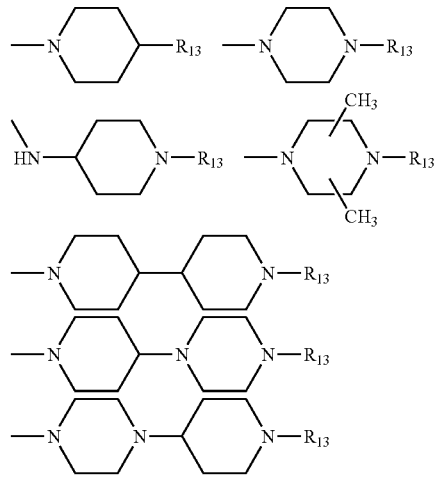

Y is selected from the group consisting of Y, COY, $(CH_2)_p Y_1$, $NR_6(CH_2)_qY_1$ and a residue selected front the group consisting of:

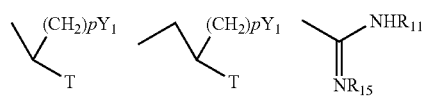

T is selected from the group consisting of $—NR_7R_8$, $—NR_{14}R_{18}R_{19}$, and $—OR_6$;

$Y_1$ is selected from the group consisting of $—NR_7R_8$, $—NR_7R_8R_{14}$ or from the following residues:

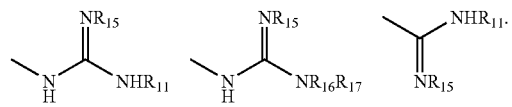

6. The compound according to claim 1, wherein the compound is selected from the group consisting of:

N-[2-[4-(2-(S)-amino-6-dimethylamino-hexanoyl)-piperazin-1-yl]-1,1-dimethyl-2-oxo-ethyl]-2,4-dichloro-3-(2-methyl -quinolin-8-yloxy-methyl)-benzensulfonamide trifluoroacetate;

N-{2-[4-(6-guanidinohexyl)-piperazin-1-yl]-1,1-dimethyl-2-oxo-ethyl}-2,4-dichloro-3-(2-methyl-8-quinolinoxymethyl) benzenesulfonamido-2-methyl-propionamide tris trifluoroacetate;

4-{2-[2,4-Dichloro-3-(2-methyl-quinolin-8-yloxymethyl)- benzene-sulfonylamino]-2-methyl-propionyl}-piperazine-1-carboxamidine;

N-[2-[4-(2-(S)-amino-5-guanidino-pentanoyl)-piperazin-1-yl]-1,1-dimethyl-2-oxo-ethyl]-2,4-dichloro-3-(2-methyl-8-quinolinoxymethyl)-benzenesulfonamide tris trifluoroacetate;

N-{2-[4-(6-aminohexyl)-piperazin-1-yl]-1,1-dimethyl-2-oxo-ethyl}-2,4-dichloro-3-(2-methyl-8-quinolinoxymethyl)-benzenesulfonamide tris trifluoroacetate;

N-{2-[4-(piperazin-2-yl)-piperazin-1-yl]-1,1-dimethyl2-oxo-ethyl}-2,4-dichloro-3-(2-methyl-8-quinolinoxymethyl)-benzenesulfonamide tris trifluoroacetate;

N-{2-[4-(piperazin-1-ylacetyl)-piperazin-1-yl]-1,1-dimethyl -2-oxo-ethyl]-2,4-dichloro-3-(2-methyl-8-quinolinoxymethyl) -benzene-sulfonamide bis trifluoroacetate;

N-{2-[4-2-(piperidin-4-yl-acetyl)-piperazin-1-yl]-1,1-dimethyl -2-oxo-ethyl}-2,4-dichloro-3-(2-methyl-8-quinolinoxymethyl) -benzene-sulfonamide bis trifluoroacetate;

N-{2-[4-[N—(4-piperidyl)glycyl]-piperazin-1-yl]-1,1-dimethyl -2-oxo-ethyl]-2,4-dichloro-3-(2-methyl-8-quinolinoxymethyl) -benzene-sulfonamide tris trifluoroacetate;

N-{2-[4-(4-(2-aminoethyl)piperazin-1-yl)acetyl) -piperazin-1-yl]-1,1-dimethyl-2-oxo-ethyl}-2,4-dichloro-3-(2-methyl-8-quinolinoxymethyl)-benzenesulfonamide tetra trifluoroacetate;

N-{2-[4-(3-(R)-Amino-6-guanidino-hexanoyl)-piperazin-1-yl]-1,1-dimethyl-2-oxo-ethyl}-2,4-dichloro-3-(2-methyl-8 -quinolinoxymethyl)-benzenesulfonamide tris trifluoroacetate;

N-{2-[4-(3-(S)-amino-6-dimethylamino-hexanoyl)-piperazin -1-yl]-1,1-dimethyl-2-oxo-ethyl}-2,4-dichloro-3-(2-methyl-8-quinolinoxymethyl)-benzenesulfonamide tris trifluoroacetate;

N-{2-[4-(3-(S)-amino-7-dimethylamino-heptanoyl)-piperazin-1-yl]-1,1-dimethyl-2-oxo-ethyl}-2,4-dichloro-3-(2-methyl-8-quinolinoxymethyl)-benzenesulfonamide tris trifluoroacetate;

N-(3-Amino-propyl)-4-{2-[2,4-dichloro-3-(2-methyl -quinolin-8-yloxy-methyl)-benzenesulfonylamino]-2-methyl-propionyl}-piperazinel-1-carboxamidine tris trifluoroacetate;

N-[2-[4-(2-(S)-amino-5-dimethylamino-pentanoyl))-piperazin-1-yl]-1,1-dimethyl-2-oxo-ethyl]-2,4-dichloro-3-(2-methyl-8-quinolinoxy-methyl)-benzenesulfonamide tris trifluoroacetate;

(S)—N-{2-[1'-(2-Amino-5-guanidino-pentanoyl)-[4,4'] Bipiperidinyl-1-yl]-1,1-dimethyl-2-oxo-ethyl}-2,4-dichloro-3-(2-methyl-quinolin-8-yloxymethyl) -benzenesulfonamide;

2,4-Dichloro—N-(2-{4-[2-(3,5-dimethyl-piperazin-1-yl) -ethyl]-3,5-dimethyl-piperazin-1-yl}-1,1-dimethyl-2-oxo-ethyl) -3-(2-methyl4a, 8a-dihydro-quinolin-8-yloxymethyl) -benzenesulfonamide;

N-(2{4-[4-(2-(S)Amino-5-guanidino-pentanoyl)-piperazin-1-yl]-piperidin-1-yl}-1,1-dimethyl-2-oxo-ethyl)-2,4-dichloro-3-(2-methyl-quinolin-8-yloxymethyl) -benzenesulfonamide;

2,4-Dichloro-3-(2,4-dimethyl-quinolin-8-yioxymethyl)-benzenesulfinic acid [1-(4-piperazin-1-yl-piperidine-1-carbonyl) -cyclopentyl]-amide;

2,4-Dichloro-3-(2,4-dimethyl-quinolin-8-yloxymethyl)-benzenesulfinic acid (1-{4-[4-(2-S-amino-6-guanidino-hexanoyl) -piperazin-1-yl]-piperidine-1-carbonyl}cyclopentyl) -amide;

2,4-Dichloro-3-(2,4-dimethyl-quinolin-8-yloxymethyl)-benzenesulfinic acid (1-{4-[4-(2-S-amino-5-guanidino-pentanoyl) -piperazin-1-yl]-piperidine-1-carbonyl}-cyclopentyl)-amide;

2,4-Dichloro-3-(2,4-dimethyl-quinolin-8-yloxymethyl)-benzenesulfinic acid [1-(4-piperidin-4yl-piperazine-1-carbonyl) -cyclopentyl]-amide;

2,4-Dichloro-3-(2-methyl-quinolin-8-yloxymethyl)-benzenesulfinic acid {2-[4-(2-guanidino-ethyl)-piperazin-1-yl]-1,1-dimethyl-2-oxo-ethyl}-amide;

2,4Dichloro-3-(2-methyl-quinolin-8-yloxymethyl)-benzenesulfinic acid (2-{4-[2-S-amino-5-(N',N"-diethyl-guanidino) -pentanoyl]-piperazin-1-yl}-1,1-dimethyl-2-oxo-ethyl) -amide;

2,4-Dichloro-3-(2-methyl-quinolin-8-yloxymethyl)-benzenesulfinic acid (2-{4-[2-R-amino-5-(N',N"-diethyl-guanidino) -pentanoyl]-piperazin-1-yl}-1,1-dimethyl-2-oxo-ethyl) -amide;

(2S)—N-(1-{4-[2-Amino-6-(N',N"-diethyl-guanidino)-hexanoyl]-piperazine-1-carbonyl}-cyclopentyl)-2,4-dichloro -3-(2,4-dimethyl-quinolin-8-yloxymethyl)-benzenesulfonamide;

N-(1-{4-[2-(S)Amino-6-(N',N"-diethyl-guanidino)-pentanoyl]-piperazine-1-carbonyl}-cyclopentyl)-2,4-dichloro -3-(2,4-dimethyl-quinolin-8-yloxymethyl)-benzenesulfonamide;

N-[2-[4-(2-(S)-Amino-6-dimethylamino-hexanoyl)-piperazn-1-yl]-1,1-dimethyl-2-oxo-ethyl]-2,4-dichloro-3-(2,4-dimethyl -quinolin-8-yloxymethyl)-benzenesulfonamide;

N-[2-[4-(3-(S)-Amino-6-dimethylamino-hexanoyl)-piperazin-1-yl]-1,1-dimethyl-2-oxo-ethyl]-2,4-dichloro-3-(2,4-dimethyl -quinolin-8-yloxymethyl)-benzenesulfonamide;

N-[2-[4-(3-(S)-Amino-6-dimethylamino-heptanoyl)-piperazin-1-yl]-1,1-dimethyl-2-oxo-ethyl]2,4-dichloro-3-(2,4-dimethyl-quinolin-8-yloxy methyl)-benzenesulfonamide;

N-[2-{4-(2-(S)Amino-5-guanidino-pentanoyl)-piperazin-1-yl]-1,1-dimethyl-2-oxo-ethyl]-2,4-dichloro-3-(2,4-dimethyl -quinolin-8-yloxymethyl)-benzenesulfonamide;

N-[2-[4-(2-(S)-Amino-6-guanidino-hexanoyl)-piperazin-1-yl]-1,1-dimethyl-2-oxo-ethyl]-2,4-dichloro-3-(2,4-dimethyl -quinolin-8-yloxymethyl)-benzenesulfonamide;

N-[2-[4-(2-(S)-Amino-5-dimethylamino-pentanoyl))-piperazin-1-yl]-1,1-dimethyl-2-oxo-ethyl]-2,4-dichloro-3-(2,4-dimethyl-quinolin-8-yloxymethyl)-benzenesulfonamide;

N-[2-[4-(2-(R)-Amino-5-guanidino-pentanoyl)-piperazin-1-yl]-1,1-dimethyl-2-oxo-ethyl]-2,4-dichloro-3-(2-methyl-quinolin-8-yloxy-methyl)-benzenesulfonamide;

N-[2-[4-(3-(S)-Amino-6-guanidino-hexanoyl)-piperazin-1-yl]1,1-dimethyl-2-oxo-ethyl]-2,4-dichloro-3-(2-methyl -quinolin-8-yloxy-methyl)-benzenesulfonamide;

N-[2-[4-(3-(S)-Amino-7-guanidino-heptanoyl)-piperazin-1-yl]-1,1-dimethyl-2-oxo-ethyl]-2,4-dichloro-3-(2-methyl -quinolin-8-yloxy-methyl)-benzenesulfonamide;

N-{2-[4-(4-2(Guanidino)ethyl]piperazin-lylacetyl) -piperazin-1-yl]-1,1-dimethyl-2-oxo-ethyl]-2,4-dichloro-3-(2-methyl-quinolin-8-yloxymethyl)-benzenesulfonamide;

N-[1-[4-(2-(S)-Amino-5-guanidino-pentanoyl)-piperazine -1-carbonyl]-cyclopentyl]-2,4-dichloro-3-(2-methyl-quluolin -8-yloxymethyl)-benzenesulfonamide tris trifluoroacetate;

N-[1-[4-(2-(S)-Amino-6-guanidino-hexanoyl)-piperazine -1-carbonyl]-cyclopentyl]-2,4-dichloro-3-(2-methyl-quinolin -8-yloxymethyl)-benzenesulfonamide tris trifluoroacetate;

N-[1-[4-(2-(S)-Amino-6-dimethylamino-hexanoyl)-piperazin -1-yl]-cyclopentyl]-2,4-dichloro-3-(2-methyl-quinolin-8-yloxymethyl)-benzenesulfonamide tris trifluoroacetate;

N-[1-[4-(2-(S)-Amino-6-guanidino-hexanoyl)-piperazine1-carbonyl]-cyclopentyl]-2,4-dichloro-3-(2,4-dimethyl-quinolin -8-yloxymethyl)-benzenesulfonamide tris trifluoroacetate;

N-[1-[4-(2-(S)-Amino-6-dimethylamino-hexanoyl)-piperazin -1-yl]-cyclopeutyl]-2,4-dichloro-3-(2,4-dimethyl-quinolin -8-yloxymethyl)-benzenesulfonamide tris trifluoroacetate;

(R)—N-[4-(2-(S)-Amino-6-guanidino-hexanoyl)-piperazine-1-carbonyl]-1-methyl-propyl]-2,4-dichloro-3-(2, 4-dimethyl -quinolin-8-yloxymethyl)-benzenesulfonamide tris trifluoroacetate;

(R)—N-[1-[4-(2-(S)-Amino-6-dimethylamino-hexanoyl) -piperazine-1-carbonyl]-1-methyl-propyl]-2,4-dichloro-3-(2,4-dimethyl-quinolin-8-yloxymethyl)-benzenesulfonamide tris trifluoroacetate;

N-{2-[4-(4-2(Guanidino)ethyl]piperazin-lylacetyl) -piperazin-1-carbonyl]-cyclopentyl]-2,4-dichloro-3-(2,4-dimethyl-quinolin-8-yloxymethyl)-benzenesulfonamide tris trifluoroacetate;

N-[1-[4-(2-(R)-Amino-6-amino-hexanoyl)-piperazine-1-carbonyl]-cyclopentyl]-2,4-dichloro-3-(2,4-dimethyl -quinolin-8-yloxymethyl)-benzenesulfonamide tris trifluoroacetate;

N-[1-[4-(2-(R)-Amino-6-guanidino-hexanoyl)-piperazine-1-carbonyl]-cyclopentyl]-2,4-dichloro-3-(2,4-dimethyl -quinolin-8-yloxymethyl)-benzenesulfonamide tris trifluoroacetate;

N-[2[4-(3-(S)-Amino-6-guanidino-hexanoyl)-piperazin-1-carbonyl]-cyclopentyl]-2,4-dichloro-3-(2,4-dimethyl -quinolin-8-yloxymethyl)-benzenesulfonamide tris trifluoroacetate;

N-[2-[4-(3-(S)-Amino-6-dimethylamino-hexanoyl)-piperazin -1-yl]-cyclopentyl]-2,4-dichloro-3-(2,4-dimethyl -quinolin-8-yloxymethyl)-benzenesulfonamide tris trifluoroacetate;

N-[1-[4-(6-Guanidino-hexanoyl)-piperazine-1-carbonyl]-cyclopentyl]-2,4-dichloro-3-(2,4-dimethyl-quinolin-8-yloxymethyl)-benzene-sulfonamide bis trifluoroacetate;

N-[2-[4-(2-(S)-Amino-6-amino-hexanoyl)-piperazin-1yl]-1,1-dimethyl-2-oxo-ethyl]-2,4-dichloro-3-(2-methyl -quinolin-8-yloxymethyl)-benzenesulfonamide tris trifluoroacetate;

N-[2-[4-(2-(S)-Guanidino-6-guanidino-hexanoyl)-piperazin -1-yl]1,1-dimethyl-2-oxo-ethyl]-2,4-dichloro-3-(2-methyl -quinolin-8-yloxy-methyl)-benzenesulfonamide tris trifluoroacetate;

(R)—N-[4-(3-(S)-Amino-6-guanidino-hexanoyl)-piperazine-1-carbonyl]-1-methyl-propyl]-2,4-dichloro-3-(2, 4-dimethyl -quinolin-8-yloxy-methyl)-benzenesulfonamide tris trifluoroacetate;

(R)—N—{2-[4-(4-2(Guanidino)ethyl]piperazin-ly-lacetyl) -piperazin-1-carbonyl]-1-methyl-propyl]-2,4-dichloro-3-(2,4-dimethyl-quinolin-8-yloxymethyl)-benzenesulfonamide tris trifluoroacetate;

(R)—N-[4-(3-(S)-Amino-6-amino-hexanoyl)-piperazine-1-carbonyl]-1-methyl-propyl]-2,4-dichloro-3-(2,4-dimethyl -quinolin-8-yloxymethyl)-benzenesulfonamide tris trifluoroacetate;

(R)—N-[4-(3-(S)-Guanidino-6-guanidino-hexanoyl) -piperazine-1-carbonyl]-1-methyl-propyl]2,4-dichloro-3-(2,4-dimethyl-quinolin-8-yloxymethyl)-benzenesulfonamide tris trifluoroacetate;

(R)—N-[4-(3-(S)-Amino-6-dimethylamino-hexanoyl) -piperazine-1-carbonyl]-1-methyl-propyl]-2,4-dichloro-3-(2,4-dimethyl-quinolin-8-yloxymethyl)-benzenesulfonamide tris trifluoroacetate;

(S)—N-[4-(2-(S)-Amino-6-guanidino-hexanoyl)-piperazine-1-carbonyl]-1-methyl-propyl]-2,4-dichloro-3-(2, 4-dimethyl -quinolin-8-yloxy-methyl)-benzenesulfonamide tris trifluoroacetate;

(S)—N-[4-(3-(S)-Amino-6-guanidino-hexanoyl)-piperazine-1-carbonyl]-1-methyl-propyl]-2,4-dichloro-3-(2, 4-dimethyl -quinolin-8-yloxy-methyl)-benzenesulfonamide tris trifluoroacetate;

2,4-Dichloro-N-{1-[4-(3(s),6-diamino-hexanoyl) -piperazine-1-carbonyl]-cyolopentyl}-3-(2,4-dimethyl -quinolin-8-yloxymethyl)-benzenesulfonamide tris trifluoroacetate;

2,4-Dichloro-N-{1-[4-(3(S), 6-diguanidino-hexanoyl) -piperazine-1-carbonyl]-cyclopentyl}-3-(2,4-dimethyl -quinolin-8-yloxymethyl)-benzenesulfonamide tris trifluoroacetate;

N-(1-{4-[3-(S),6-Bis-(N',N''-dicyclohexyl-guanidino) -hexanoyl]-piperazine-1-carbonyl}-cyclopentyl)-2,4-dichloro-3-(2,4-dimethyl-quinolin-8-yloxymethyl) -benzensulfonamide tris trifluoroacetate;

N-{1-[4-(2-(S)Amino-3-piperidin-4yl-propionyl) -piperazine-1-carbonyl]-cyclopentyl}-2,4-dichloro-3-(2,4-dimethyl-quinolin-8-yloxymethyl)-benzenesulfonamide tris trifluoroacetate;

N-{1-[4-(2-Trimethylammonium-acetyl)-piperazine-1-carbonyl]-cyclopentyl}-2,4-dichloro-3-(2,4-dimethyl -quinolin-8-yloxymethyl)-benzenesulfonamide bis trifluoroacetate;

N-{1-[4-(4-Trimethylammonium-butanoyl)-piperazine-1-carbonyl]-cyclopentyl}-2,4-dichloro-3-(2,4-dimethyl -quinolin-8-yloxymethyl)-benzenesulfonamide bis trifluoroacetate;

N-{1-[4-(3(R)-Hydroxy-4-trimethylammonium-butanoyl) -piperazine-1-carbonyl]-cyclopentyl}-2,4-dichloro-3-(2,4-dimethyl-quinolin-8-yloxy-methyl)-benzenesulfonamide bis trifluoroacetate;

N-[1-[4-(2-(S)-Dimethylamino-6-dimethylamino-hexanoyl) -piperazin-1-yl]-cyclopentyl]-2,4-dichloro-3-(2, 4-dimethyl-quinolin-8-yloxy-methyl)-benzenesulfonamide tris trifluoroacetate;

{5-[(1-{1-[2,4-Dichloro-3-(2,4-dimethyl-quinolin-8-yloxymethyl) -benzensulfonylamino]-cyclopentanecarbonyl}-piperidin-4-ylmethyl)-dimethyl-ammonium] pentyl}-trimethyl-ammonium tris trifluoroacetate;

{5-[(1-{1-[2,4-Dichloro-3-(2,4-dimethyl-quinolin-8-yloxymethyl) -benzensulfonylamino]-cyclopentanecarbonyl}-piperidine-4-carbonyl)-amino]-pentyl}-trimethyl-ammonium bis trifluoroacetate;

N-[1-[4-2-(S)-Trimethylammonium-6-trimethylammonium-hexanoyl) -piperazin-1-yl]-cyclopentyl]-2,4-dichloro-3-(2,4-dimethyl-quinolin-8-yloxymethyl)-benzenesulfonamide tris trifluoroacetate;

N-[1-[4-(2-(R)-Trimethylammonium-6-trimethylammonium-hexanoyl) piperazin-1-yl]-cyclopentyl]-2,4-dichloro-3-(2,4-dimethyl-quinolin-8-yloxymethyl)-benzenesulfonamide tris trifluoroacetate;

N-[1-[4-(2-(S)-Trimethylammonium-6-amino-hexanoyl)-piperazin-1-yl]-cyclopentyl]-2,4-dichloro-3-(2,4-dimethyl-quinolin-8-yloxymethyl)-benzenesulfonamide tris trifluoroacetate;

N-{1-[4-(6-Trimethylammonium-hexanoyl)-piperazine-1-carbonyl]-cyclopentyl}-2,4-dichloro-3-(2,4-dimethyl-quinolin-8-yloxymethyl)-benzenesulfonamide bis trifluoroacetate;

N-(6-Amino-hexyl)-4-{2-[2,4-dichloro-3-(2-methyl-quinolin-8-yloxy-methyl)-benzenesulfonylamino]-2-methyl-propionyl}-piperazine-1-carboxamidine;

N-[2-(3-Amino-propylamino)-ethyl]-4-{2-[2,4-dichloro-3-(2-methyl-quinolin-8-yloxymethyl)-benzenesulfonylamino]-2-methyl-propionyl}-piperazine-1-carboxamidine;

N-(3-Amino-propyl)-4-{2-[2,4-dichloro-3-(2,4-dimethyl-quinolin-8-yloxymethyl)-benzenesulfonylamino]-2-methyl-propionyl}-piperazine-1-carboxamidine bis trifluoroacetate;

N-(6-Amino-hexyl)-4-{1-[2,4-dichloro-3-(2,4-dimethyl-quinolin-8-yloxymethyl)-benzenesulfonylamino]-cyclopentanecarbonyl}-piperazine-1-carboxamidine bis trifluoroacetate;

N-[2-(3-Amino-propylamino)-ethyl]-4-{1-[2,4-dichloro-3-(2,4-dimethyl-quinolin-8-yloxymethyl)-benzenesulfonylamino]-cyclo-pentanecarbonyl}-piperazine-1-carboxamidine bis trifluoroacetate:

N-[2-(4-{1-[2,4-Dichloro-3-(2,4-dimethyl-quinolin-8-yloxymethyl)-benzenesulfonylamino]-cyclopentanecarbonyl}-piperazin-1-yl)-ethyl]-4-methyl-piperazine-1-carboxamidine bis trifluoroacetate;

2,4Dichloro-N-{1-[4-(2(R),6-diamino-hexyl)-piperazine-1-carbonyl]-cyclopentyl}-3-(2,4-dimethyl-quinolin-8-yloxymethyl)-benzene-sulfonamide tetra trifluoroacetate;

2,4-Dichloro-N-{1-[4-(2(R),6-diguanidino-hexyl)-piperazine-1-carbonyl]-cyclopentyl}-3-(2,4-dimethyl-quinolin-8-yloxymethyl)-benzenesulfonamide tetrahydrochloride 2,4-Dichloro-3-(2,4-dimethyl-quinolin-8-yloxymethyl)-N-{1-[4-(2-piperazin-1yl-ethyl)-piperazine-1-carbonyl]-cyclopentyl}-benzenesulfonamide tetra trifluoroacetate;

2,4-Dichloro-3-(2,4-dimethyl-quinolin-8-yloxymethyl)-N-{1-[4-(2-piperidin-4-yl-ethyl)-piperazine-1-carbonyl]-cyclopentyl}-benzene-sulfonamide;

{3-[(4-{1-[2,4-Dichloro-3-(2,4-dimethyl-quinolin-8-yloxymethyl)-benzenesulfonylamino]-cyclopentanecarbonyl}-piperazine-1-carboximi-doyl)-amino]propyl}-trimethyl-ammonium iris trifluoroacetate;

4-{1-[2,4-Dichloro-3-(2,4-dimethyl-quinolin-8-yloxymethyl)-benzene-sulfonylaminol]-cyclopentanecarbonyl}-N-(3-dimethylamino-propyl)-piperazine-1-carboxamidine tris trifluoroacetate;

N-(1-{4-[(5-Amino-pentylamino)-methyl]-piperidine-1-carbonyl}-cyclopentyl)-2,4-dichloro-3-(2,4-dimethyl-quinolin-8-yloxymethyl)-benzenesulfonamide tris trifluoroacetate;

N-{1-(4-(4-Amino-piperidin-1-ylmethyl)-piperidine-1-carbonyl]-cyclopentyl}-2,4-dichloro-3-(2,4-dimethyl-quinolin-8-yloxymethyl)-benzenesulfonamide tris trifluoroacetate;

2,4-Dichloro-3-(2,4-dimethyl-quinolin-8-yloxymethyl)-N-(1-{4-[(5-methylamino-pentylamino)-methyl]-piperidine-1-carbonyl}-cyclopentyl)-benzenesulfonamide tris trifluoroacetate; and Amino-6-(4-{1-(2,4-dichloro-3-(2,4-dimethyl-quinolin-8-yloxymethyl)-benzenesulfonylamino]-cyclopentanecarbonyl}-piperazin-1-yl)-6-oxo-hexyl]-trimethyl-ammonium bis trifluoroacetate.

7. An intermediate of general formula (6) or (7)

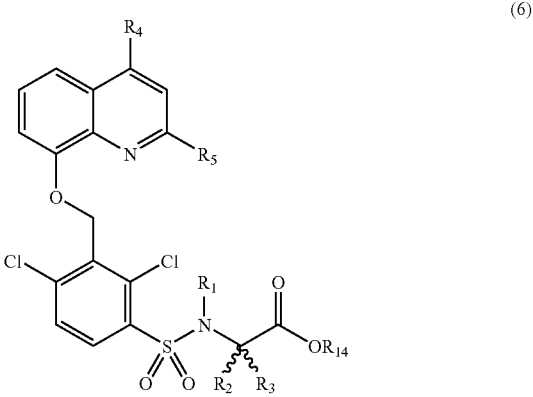

(6)

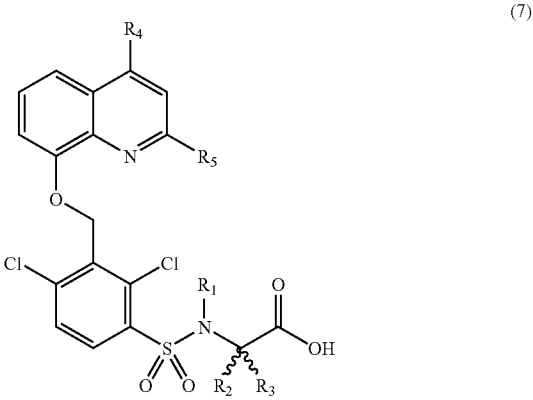

(7)

in which $R_1$ can be H or methyl, $R_2$ and $R_3$ can be independently methyl, ethyl or, together with the carbon atom which they are linked to, form a cyolopentyl group, and $R_{14}$ is methyl or t-butyl.

8. An intermediates of general formula (1)

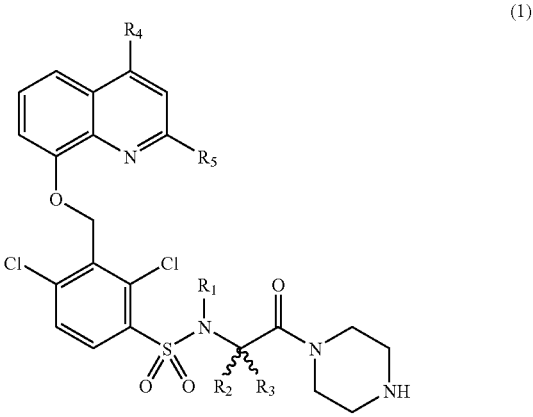

(1)

in which $R_1$ can be H or methyl, $R_2$ and $R_3$ can be independently methyl, ethyl or, together with the carbon atom which they are linked to, form a cyclopentyl group.

9. A pharmaceutical composition containing as an active ingredient a compound as claimed in any one of claims 1 to 6, together with pharmaceutically acceptable excipients.

10. A method for the treatment of inflammation, asthma, chronic bronchitis, allergic rhinitis or obstructive pulmonary disease (COPD) in a subject in need thereof, which comprises administering to said subject a therapeutically effective amount of a compound according to claim 1.

* * * * *